(12) United States Patent
Wada et al.

(10) Patent No.: US 11,020,202 B2
(45) Date of Patent: Jun. 1, 2021

(54) IMAGE PROCESSING DEVICE, IMAGE PROCESSING METHOD, AND SURGICAL NAVIGATION SYSTEM

(71) Applicant: SONY CORPORATION, Tokyo (JP)

(72) Inventors: Seiji Wada, Kanagawa (JP); Yasuaki Takahashi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 148 days.

(21) Appl. No.: 16/314,461

(22) PCT Filed: Apr. 24, 2017

(86) PCT No.: PCT/JP2017/016163
§ 371 (c)(1),
(2) Date: Dec. 31, 2018

(87) PCT Pub. No.: WO2018/012080
PCT Pub. Date: Jan. 18, 2018

(65) Prior Publication Data
US 2019/0151043 A1     May 23, 2019

(30) Foreign Application Priority Data
Jul. 12, 2016   (JP) .............................. JP2016-138035

(51) Int. Cl.
*G06K 9/00*     (2006.01)
*A61B 5/05*     (2021.01)
(Continued)

(52) U.S. Cl.
CPC ............ *A61B 90/36* (2016.02); *A61B 5/0042* (2013.01); *A61B 5/489* (2013.01); *A61B 6/12* (2013.01);
(Continued)

(58) Field of Classification Search
USPC ........ 382/100, 103, 128–134, 154–156, 162, 382/168, 173, 181, 189, 199, 219, 224,
(Continued)

(56) References Cited

U.S. PATENT DOCUMENTS 5,633,951 A * 5/1997 Moshfeghi ........... G06K 9/6207
                                                   375/E7.084
5,954,648 A * 9/1999 Van Der Brug ....... A61B 90/13
                                                   600/411
(Continued)

FOREIGN PATENT DOCUMENTS

CN       1964676 A      5/2007
CN     103443825 A     12/2013
(Continued)

OTHER PUBLICATIONS

International Search Report and Written Opinion of PCT Application No. PCT/JP2017/016163, dated Jul. 25, 2017, 08 pages of ISRWO.

(Continued)

*Primary Examiner* — Seyed H Azarian
(74) *Attorney, Agent, or Firm* — Chip Law Group

(57) ABSTRACT

Provided is an image processing device including a matching unit that performs matching processing between a predetermined pattern on a surface of a 3D model of a biological tissue including an operating site generated on the basis of a preoperative diagnosis image and a predetermined pattern on a surface of the biological tissue included in a captured image during surgery, a shift amount estimation unit that estimates an amount of deformation from a preoperative state of the biological tissue on the basis of a result of the matching processing and information regarding a three-dimensional position of a photographing region which is a region photographed during surgery on the surface of the biological tissue, and a 3D model update unit that updates (Continued)

the 3D model generated before surgery on the basis of the estimated amount of deformation of the biological tissue.

16 Claims, 12 Drawing Sheets

(51) Int. Cl.
| | |
|---|---|
| A61B 90/00 | (2016.01) |
| A61B 6/00 | (2006.01) |
| G06T 7/00 | (2017.01) |
| G06T 15/08 | (2011.01) |
| G06T 17/20 | (2006.01) |
| A61B 6/12 | (2006.01) |
| G16H 30/00 | (2018.01) |
| A61B 5/00 | (2006.01) |
| G06T 7/50 | (2017.01) |
| A61B 34/20 | (2016.01) |
| A61B 90/20 | (2016.01) |
| G06T 7/33 | (2017.01) |
| G06T 7/593 | (2017.01) |
| A61B 90/30 | (2016.01) |
| A61B 90/25 | (2016.01) |
| A61B 6/03 | (2006.01) |
| A61B 5/055 | (2006.01) |
| A61B 34/10 | (2016.01) |
| A61B 17/00 | (2006.01) |

(52) U.S. Cl.
CPC .............. *A61B 6/501* (2013.01); *A61B 6/504* (2013.01); *A61B 6/5217* (2013.01); *A61B 34/20* (2016.02); *A61B 90/20* (2016.02); *A61B 90/37* (2016.02); *G06T 7/00* (2013.01); *G06T 7/337* (2017.01); *G06T 7/50* (2017.01); *G06T 7/593* (2017.01); *G06T 15/08* (2013.01); *G06T 17/20* (2013.01); *G16H 30/00* (2018.01); *A61B 5/0071* (2013.01); *A61B 5/055* (2013.01); *A61B 5/742* (2013.01); *A61B 5/746* (2013.01); *A61B 6/03* (2013.01); *A61B 6/5205* (2013.01); *A61B 90/25* (2016.02); *A61B 2017/00119* (2013.01); *A61B 2034/102* (2016.02); *A61B 2034/105* (2016.02); *A61B 2034/2055* (2016.02); *A61B 2034/2057* (2016.02); *A61B 2034/2059* (2016.02); *A61B 2034/2065* (2016.02); *A61B 2090/061* (2016.02); *A61B 2090/309* (2016.02); *A61B 2090/365* (2016.02); *A61B 2090/367* (2016.02); *A61B 2090/371* (2016.02); *A61B 2090/373* (2016.02); *A61B 2090/374* (2016.02); *A61B 2090/3762* (2016.02); *A61B 2576/026* (2013.01); *G06T 2207/10056* (2013.01); *G06T 2207/30016* (2013.01); *G06T 2207/30101* (2013.01)

(58) Field of Classification Search
USPC ....... 382/254, 274, 276, 285–291, 305, 312; 600/411; 375/E7.084
See application file for complete search history.

(56) References Cited

U.S. PATENT DOCUMENTS

| | | | |
|---|---|---|---|
| 9,668,710 B2 * | 6/2017 | Ruijters | ................ A61B 6/461 |
| 2005/0101855 A1 | 5/2005 | Miga et al. | |
| 2008/0051651 A1 | 2/2008 | Yamamoto et al. | |
| 2011/0054300 A1 * | 3/2011 | Yamamoto | .............. A61B 90/36 |
| | | | 600/411 |
| 2012/0010498 A1 * | 1/2012 | Yamamoto | ............... A61B 8/08 |
| | | | 600/411 |
| 2014/0003698 A1 * | 1/2014 | Ruijters | ................. A61B 6/461 |
| | | | 382/131 |

FOREIGN PATENT DOCUMENTS

| | | |
|---|---|---|
| EP | 1738709 A1 | 1/2007 |
| JP | 2005-278992 A | 10/2005 |
| JP | 2007-209531 A | 8/2007 |
| JP | 2013-202313 A | 10/2013 |
| JP | 2014-512210 A | 5/2014 |
| JP | 2017-113343 A | 6/2017 |
| WO | 2005/094713 A1 | 10/2005 |
| WO | 2012/127345 A1 | 9/2012 |

OTHER PUBLICATIONS

Office Action for JP Patent Application No. 2018-527403 dated Dec. 1, 2020, 03 pages of Office Action and 03 pages of English Translation.

* cited by examiner

IMAGE PROCESSING DEVICE, IMAGE PROCESSING METHOD, AND SURGICAL NAVIGATION SYSTEM

CROSS REFERENCE TO RELATED APPLICATIONS

This application is a U.S. National Phase of International Patent Application No. PCT/JP2017/016163 filed on Apr. 24, 2017, which claims priority benefit of Japanese Patent Application No. JP 2016-138035 filed in the Japan Patent Office on Jul. 12, 2016. Each of the above-referenced applications is hereby incorporated herein by reference in its entirety.

TECHNICAL FIELD

The present disclosure relates to an image processing device, an image processing method, a program, and a surgical navigation system.

BACKGROUND ART

A surgical navigation system that supports a surgeon by presenting a positional relationship between an operating site of a patient and a treatment tool at the time of surgery to a surgeon has been developed. For example, in the technique described in Patent Literature 1, a 3D model of the biological tissue is generated based on tomography images of a biological tissue including the operating site of the patient acquired before surgery. Then, at the time of surgery, three-dimensional positions of the biological tissue and the treatment tool are detected and a navigation image in which a display indicating the position of the treatment tool is added to the 3D model is caused to be displayed, for example, on a display device set in a surgery room. According to the technology, since the surgeon can perform surgery while ascertaining a distance between the operating site and the treatment tool, a distance between a part in which contact with the treatment tool in the biological tissue needs to be avoided and the treatment tool, and the like using the navigation image, smoother surgery can be executed and it is possible to improve the convenience of a surgeon.

CITATION LIST

Patent Literature

Patent Literature 1: JP 2013-202313A

DISCLOSURE OF INVENTION

Technical Problem

However, the actual position and shape of the biological tissue of a patient at the time of surgery may change from those before surgery due to changes in the position of the patient or influence and the like of treatment such as a laparotomy or craniotomy according to the surgery. In other words, the position and shape of the biological tissue of the patient at the time of surgery does not necessarily coincide with a 3D model generated based on information acquired before surgery. In such a case, according to the technology described in Patent Literature 1, the accurate position and shape of the biological tissue in conformity with a current state are not reflected in the navigation image, and the positional relationship between the biological tissue and the treatment tool is not accurately displayed. Therefore, appropriate navigation cannot be performed, and the convenience of a surgeon may be degraded.

In view of this, the present disclosure proposes a novel and improved image processing device, image processing method, program and surgical navigation system which can further improve the convenience of a user.

Solution to Problem

According to the present disclosure, there is provided an image processing device including: a matching unit that performs matching processing between a predetermined pattern on a surface of a 3D model of a biological tissue including an operating site generated on the basis of a preoperative diagnosis image and a predetermined pattern on a surface of the biological tissue included in a captured image during surgery; a shift amount estimation unit that estimates an amount of deformation from a preoperative state of the biological tissue on the basis of a result of the matching processing and information regarding a three-dimensional position of a photographing region which is a region photographed during surgery on the surface of the biological tissue; and a 3D model update unit that updates the 3D model generated before surgery on the basis of the estimated amount of deformation of the biological tissue.

In addition, according to the present disclosure, there is provided an image processing method including: performing, by a processor, matching processing between a predetermined pattern on a surface of a 3D model of a biological tissue including an operating site generated on the basis of a preoperative diagnosis image and a predetermined pattern on a surface of the biological tissue included in a captured image during surgery; estimating an amount of deformation from a preoperative state of the biological tissue on the basis of a result of the matching processing and information regarding a three-dimensional position of a photographing region which is a region photographed during surgery on the surface of the biological tissue; and updating the 3D model generated before surgery on the basis of the estimated amount of deformation of the biological tissue.

In addition, according to the present disclosure, there is provided a program that causes a computer to execute an image processing method including: performing matching processing between a predetermined pattern on a surface of a 3D model of a biological tissue including an operating site generated on the basis of a preoperative diagnosis image and a predetermined pattern on a surface of the biological tissue included in a captured image during surgery; estimating an amount of deformation from a preoperative state of the biological tissue on the basis of a result of the matching processing and information regarding a three-dimensional position of a photographing region which is a region photographed during surgery on the surface of the biological tissue; and updating the 3D model generated before surgery on the basis of the estimated amount of deformation of the biological tissue.

In addition, according to the present disclosure, there is provided a surgical navigation system including: a microscope unit that photographs a biological tissue including an operating site of a patient during surgery, and acquires a captured image with depth information; a position sensor that detects three-dimensional positions of the microscope unit, the patient, and a treatment tool; a display device that displays a navigation image in which a display indicating a position of the treatment tool is added to a 3D model of the biological tissue; and an image processing device that causes the display device to display the navigation image. The image processing device includes a matching unit that performs matching processing between a predetermined pattern on a surface of the 3D model generated on the basis of a preoperative diagnosis image and a predetermined pattern on a surface of the biological tissue included in a captured image during surgery, a shift amount estimation unit that estimates an amount of deformation from a preoperative state of the biological tissue on the basis of a result of the matching processing and information regarding a three-dimensional position of a photographing region which is a region photographed during surgery by the microscope unit on the surface of the biological tissue, a 3D model update unit that updates the 3D model generated before surgery on the basis of the estimated amount of deformation of the biological tissue, and a display control unit that causes the display device to display the navigation image using the updated 3D model. Information regarding a three-dimensional position of the photographing region is acquired on the basis of a result of detection by the position sensor and depth information of a captured image by the microscope unit.

According to the present disclosure, in regard to a 3D model of a biological tissue including an operating site generated on the basis of information acquired before surgery and a captured image at the time of actual surgery, matching processing between an image representing a pattern on a surface of the 3D model and an image representing a pattern on a surface of the biological tissue included in the captured image is performed. Then, an amount of deformation from a state of the biological tissue before the surgery is estimated on the basis of a result of the matching processing, and the 3D model is updated on the basis of a result of the estimation. As a result, the updated 3D model reflects the actual position and shape of the biological tissue at the time of surgery, and thus if a navigation image is generated using the updated 3D model, a more accurate navigation image conforming to an actual situation can be obtained. Therefore, it is possible to further improve the convenience of a user who performs surgery using the navigation system.

Advantageous Effects of Invention

According to the present disclosure, convenience of a user can be further improved. Note that the effects described above are not necessarily limitative. With or in the place of the above effects, there may be achieved any one of the effects described in this specification or other effects that may be learned from this specification.

MODE(S) FOR CARRYING OUT THE INVENTION

Figure 1:
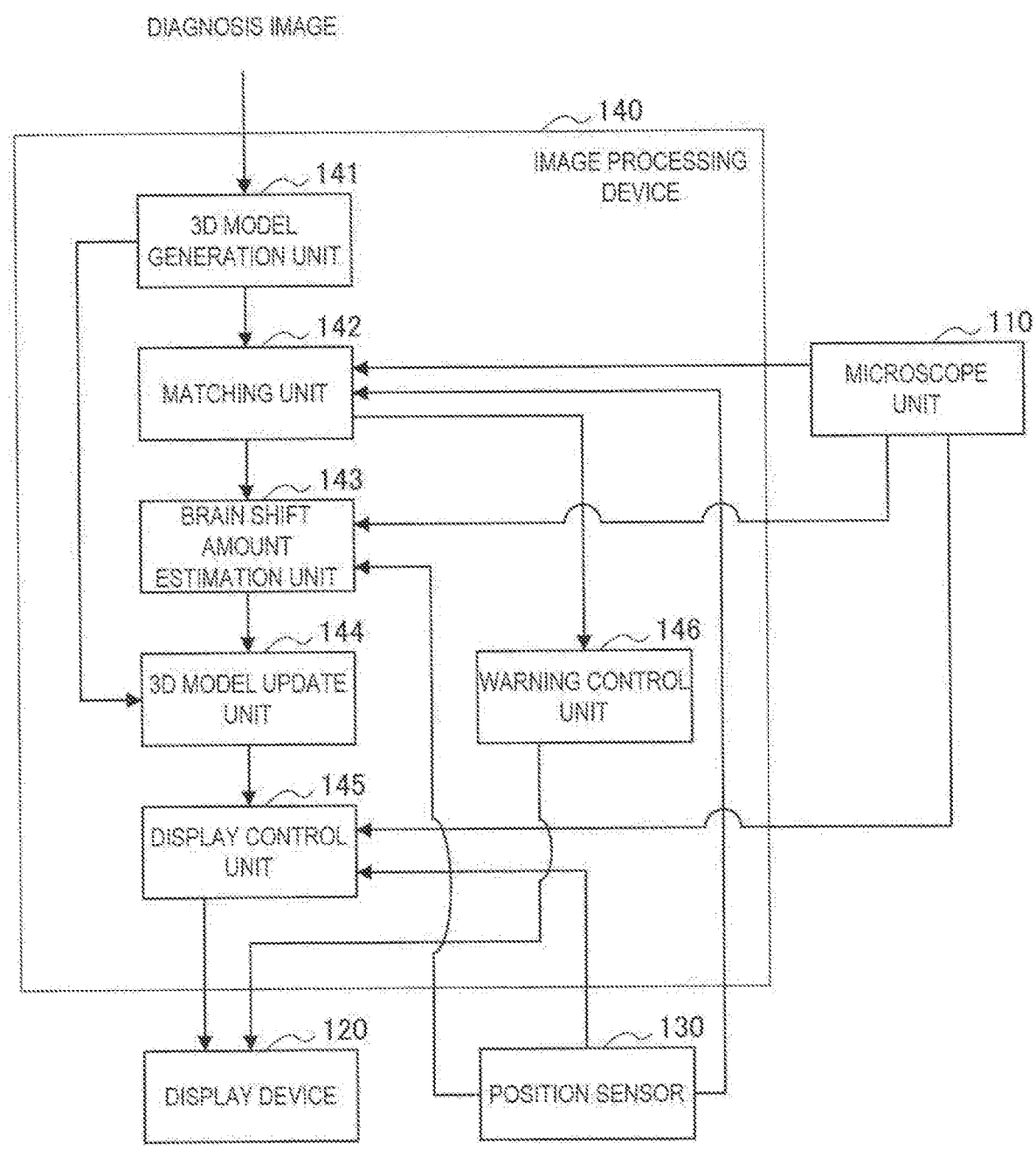
FIG. 1 is a block diagram which shows an example of a configuration of a surgical navigation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that the description will be made in the following order.
1. Background of the present disclosure
2. Configuration of surgical navigation system
3. Image processing method
4. Configuration example of observation device
5. Application example
6. Supplement Here, as an example, an embodiment in which a technology according to the present disclosure is applied to a brain surgical operation will be described in the following description. However, the present disclosure is not limited to such an example. The technology according to the present disclosure may also be applied to other types of surgery.

In addition, a user who uses a surgery support system to be described below is described as a surgeon for the sake of convenience in the following description. However, this description does not limit the user using the surgery support system, and a subject using the surgery support system may also be another medical staff member such as an assistant or a nurse.

1. Background of the Present Disclosure

Before describing preferred embodiments of the present disclosure, the inventors will describe the background of the present disclosure to make the present disclosure clearer.

In a brain surgical operation, surgery is performed while observing an operating site of a patient in an enlarged manner through a microscope unit. For such a brain surgical operation, a surgical navigation system as described in Patent Literature 1 described above has been developed. In the surgical navigation system, a diagnostic image of a patient's brain is photographed by using computed tomography (CT) or magnetic resonance imaging (MRI) before surgery. Then, a 3D model of the brain is generated on the basis of the photographed diagnostic image. At the time of surgery, three-dimensional positions of a microscope unit, a patient, and a treatment tool are detected by a position sensor, and a navigation image in which a display indicating a region corresponding to a current field of view of the microscope unit or a display indicating a position of the current treatment tool is added to the 3D model is displayed on a display device installed in a surgery room on the basis of a result of the detection. According to such a surgical navigation system, since a positional relationship between the operating site (for example, a lesion to be resected) and the treatment tool can be displayed in real time in the navigation image, a surgeon can perform surgery while ascertaining the positional relationship.

For example, the operating site may be hardly distinguishable in appearance from other normal tissues in some cases. In such a case, by reflecting the position of the operating site obtained by a prior examination of the 3D model, the surgeon can ascertain the positional relationship between the operating site and the treatment tool, which is difficult to discern with the naked eye, on the navigation image, and thus it is very useful. In addition, since positions of blood vessels inside the brain can also be reflected in the 3D model, positional relationships between the blood vessels and the treatment tool can be displayed on the navigation image. Therefore, for example, when the surgeon incises the brain and causes the operating site to be exposed, a risk of accidentally damaging the blood vessels can be reduced by referring to the navigation image.

However, it is known that a phenomenon known as brain shift in which the brain, the shape of which is normally maintained by the cranial bone or cerebrospinal fluid, loses support in a craniotomy and the shape thereof changes occurs in a brain surgical operation. When brain shift occurs, a 3D model generated on the basis of information obtained before surgery differs from the shape of brain at the time of actual surgery, and thus a 3D model that accurately reflects the brain is not displayed in the navigation image. Therefore, the positional relationship between the operating site and the treatment tool and the positional relationship between the blood vessels and the treatment tool as described above cannot be accurately represented in the navigation image, which makes it difficult to perform appropriate navigation.

Therefore, as one countermeasure against brain shift, CT photography or MRI photography is performed during surgery (so-called intraoperative CT photography or intraoperative MRI photography), and a technology for updating a 3D model displayed in a navigation image on the basis of the obtained diagnostic image has been proposed. According to this method, the 3D model reflecting the shape of the brain after brain shift is displayed in the navigation image, and it is possible to perform navigation conforming to the actual situation.

However, in order to perform the intraoperative CT photography or the intraoperative MRI photography, it is necessary to install a dedicated CT device or MRI device in the surgery room or to arrange the surgery room and a CT room or an MRI room side by side, and thus cost for introduction is high. In addition, in order to perform the intraoperative CT photography or the intraoperative MRI photography, it is necessary to suspend surgery and perform the photography processing, and thus there are concerns that work is complicated, time for surgery increases, and a burden patient increases.

Therefore, the inventors have conducted intensive studies on a technology capable of further improving the convenience of a surgeon by obtaining an appropriate navigation image more easily in a surgical operation, particularly in a brain surgical operation. The present disclosure was conceived as a result of this. Hereinafter, preferred embodiments of the present disclosure that the inventors have conceived of will be described.

2. Configuration of Surgical Navigation System

With reference to FIG. 1, a configuration according to a preferred embodiment of the present disclosure will be described. FIG. 1 is a block diagram which shows an example of a configuration of a surgical navigation system according to the present embodiment.

With reference to FIG. 1, a surgical navigation system 10 according to the present embodiment includes a microscope unit 110, a display device 120, a position sensor 130, and an image processing device 140.

(Microscope Unit)

The microscope unit 110 is a means for observing an operating site in an enlarged manner. The microscope unit 110 is configured with an image sensor, an optical system for guiding light from an observation target (observation light) to the image sensor, and the like accommodated in a housing. The image sensor generates a signal corresponding to the observation light, i.e., an image signal corresponding to an observation image, by receiving and photoelectrically converting the observation light. As described, the microscope unit 110 is an electronic imaging microscope unit that electronically photographs images. In addition, the microscope unit 110 is configured to photograph an image including depth information. For example, the microscope unit 110 has an auto focus (AF) function, and the microscope unit 110 can acquire depth information of a position which is in focus within an angle of view on the basis of information regarding a focal distance.

In the brain surgical operation, a part of the cranial bone of a patient is craniotomized, and the surface of the brain exposed from the open head is photographed by the microscope unit 110. The microscope unit 110 transmits an image signal according to an acquired captured image, that is, information regarding the captured image, to the image processing device 140 (specifically, the matching unit 142, the brain shift amount estimation unit 143, and the display control unit 145 of the image processing device 140 to be described below).

Note that the microscope unit 110 obtains depth information regarding the basis of a focal distance, but the present embodiment is not limited to such an example. The microscope unit 110 may be capable of photographing a captured image to which the depth information is added, and a configuration thereof may be arbitrary. For example, a distance measurement sensor may also be provided in the microscope unit 110. As the distance measurement sensor, for example, various types of sensors such as time-of-flight type sensors or laser scan type sensors may be used. According to the method, it is possible to measure a three-dimensional position of brain surface blood vessels more accurately than in the case of using a focal distance. Alternatively, the microscope unit 110 may be configured as a stereo camera, and depth information may also be obtained on the basis of disparity information. However, since a configuration of the microscope unit 110 becomes complicated in a case in which a distance measurement sensor or a stereo camera is used, the method of using a focal distance is preferable to more easily obtain depth information.

In addition, in the present embodiment, the microscope unit 110 can be supported by an arm unit. In addition, an actuator is provided in each joint unit of the arm unit, an attitude of the arm unit is controlled by the actuator being driven, and the position and attitude of the microscope unit 110 can be controlled. A specific configuration of a support arm device (observation device) that supports the microscope unit 110 will be described in the following description (4. Configuration example of observation device).

(Display Device)

The display device 120 is installed at a position at which it is visible to a surgeon in a surgery room. A captured image of an operating site photographed by the microscope unit 110 is displayed on the display device 120 by control from the image processing device 140. The surgeon performs various types of treatments on an operating site while observing the operating site according to a captured image displayed on the display device 120.

Moreover, a navigation image in which a display indicating a position of a current treatment tool is added to a 3D model of the brain is displayed in the display device 120 under a control of the image processing device 140. A surgeon performs surgery while ascertaining a positional relationship between the brain and the treatment tool (specifically, a positional relationship between a blood vessel and the treatment tool, a positional relationship between an operating site and the treatment tool, and the like) according to the navigation image displayed on the display device 120. Note that the details of a navigation image will be described below with reference to FIGS. 10 and 11.

A specific configuration of the display device 120 is not limited, and as the display device 120, various known display devices, for example, a liquid crystal display device, an electro-luminescence (EL) display device, or the like, may be applied.

Note that, although only one block showing the display device 120 is illustrated in FIG. 1 for the sake of convenience, a plurality of display devices 120 may also be provided in the surgical navigation system 10. In a case in which the plurality of display devices 120 are used, a captured image and a navigation image of an operating site can be displayed on separate display devices 120. Alternatively, in a case in which only one display device 120 is used, a display screen of the display device 120 is divided into two areas, and an operating site image and a navigation image can be displayed separately in these areas.

(Position Sensor)

Figure 2:
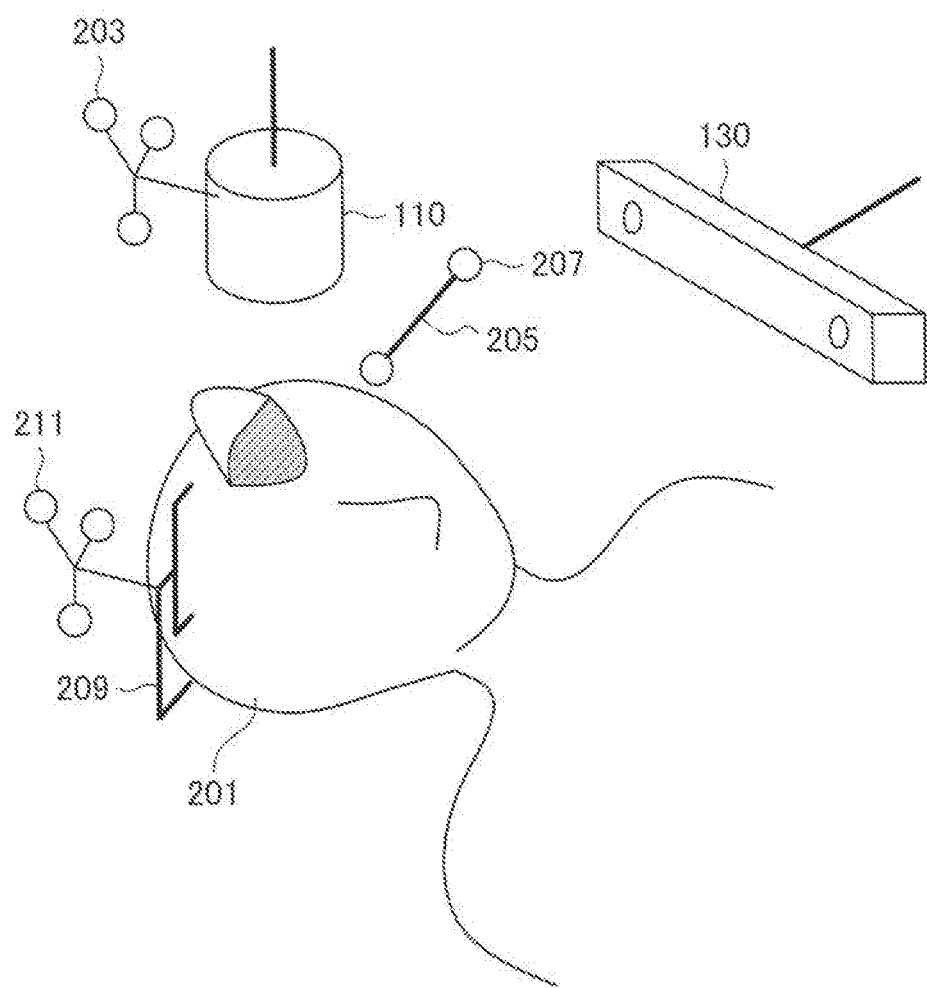
FIG. 2 is a diagram for describing a function of a position sensor.

The position sensor 130 detects three-dimensional positions of a patient's head, the microscope unit 110, and a treatment tool. FIG. 2 is a diagram for describing a function of the position sensor 130. FIG. 2 schematically shows a positional relationship among a patient 201, the microscope unit 110, a treatment tool 205, and the position sensor 130.

As shown in FIG. 2, markers 203 and 207 are attached to the microscope unit 110 and the treatment tool 205. In addition, a marker 211 is also attached to the head of the patient 201 via a support member 209. The position sensor 130 is configured as a stereo camera, and can detect three-dimensional positions of markers 203, 207 and 211, that is, the three-dimensional positions of the head of the patient 201, the microscope unit 110, and a three-dimensional position of the treatment tool 205, on the basis of a captured image thereof.

The position sensor 130 transmits information regarding the detected three-dimensional positions of the head of the patient 201, the microscope unit 110, and the treatment tool 205 to the image processing device 140 (specifically, a matching unit 142, a brain shift amount estimation unit 143, and a display control unit 145 of the image processing device 140 to be described below).

Note that a configuration of the position sensor 130 is not limited to such an example, and various types of known sensors capable of detecting a three-dimensional position of an object may be used as the position sensor 130. For example, the markers 203, 207, and 211 may be magnets, and a magnetic sensor may be used as the position sensor 130.

(Image Processing Device)

The image processing device 140 performs various types of display control in the surgical navigation system 10. Hereinafter, functional units of the image processing device 140 will be described in detail. The image processing device 140 includes a 3D model generation unit 141, a matching unit 142, a brain shift amount estimation unit 143, a 3D model update unit 144, and a display control unit 145 as the functional units thereof. Note that the image processing device 140 can be, for example, a processor such as a central processing unit (CPU), a graphics processing unit (GPU), or the like, a control board on which memory elements such as processors and memories are mixed, a general information processing device such as a personal computer (PC), or the like, on which a processor is mounted. When a processor included in the image processing device 140 executes an arithmetic operation process in accordance with a predetermined program, each of the above-described functions can be realized.

In the surgical navigation system 10, diagnostic images of a patient's brain are photographed before surgery, and information regarding these diagnostic images is managed to be accessed by the image processing device 140. The 3D model generation unit 141 generates a 3D model of the brain on the basis of the diagnostic images acquired before surgery.

As a diagnostic image for generating a 3D model, any image used at the time of diagnosis may be generally applied. However, as will be described below, a 3D model of the brain generated by the 3D model generation unit 141 is used for the navigation image. Therefore, it is preferable that the diagnostic image be an image in which an operating site is clearly represented (that is, a disease emphasis image) such that a position of the operating site can be indicated on the 3D model. In addition, as will be described below, in the 3D model of the brain generated by the 3D model generation unit 141, an image representing a pattern of blood vessels (a blood vessel pattern image) is extracted from the 3D model, and used in matching processing of blood vessel pattern images. Therefore, it is preferable that the diagnostic image be an image in which the shape of the blood vessels is clearly represented (that is, a blood vessel emphasis image). In the present embodiment, one or a plurality of diagnostic images can be used in the generation of a 3D model in consideration of these points. For example, as the diagnostic image, an image photographed by MRI, magnetic resonance angiography (MRA), 3D-CT angiography (CD-CTA), 3D-digital subtraction angiography (3D-DSA), single photon emission CT (SPECT), and the like can be used.

The 3D model generation unit 141 generates a 3D model by converting tomography images for each composition obtained by each method such as MRI into a 3D model using, for example, a technology such as volume rendering (VR) or surface rendering (SR) following a continuity of each composition. The processing of generating a 3D model using the 3D model generation unit 141 may be performed using various types of known methods, and thus the detailed description thereof will be omitted.

The 3D model generation unit 141 provides information regarding a generated 3D model of the brain to the matching unit 142 and the 3D model update unit 144.

The matching unit 142 calculates a three-dimensional position on the surface of the brain during surgery by matching feature points of an image representing a blood vessel pattern of the brain surface included in a 3D model of the brain generated by the 3D model generation unit 141 (hereinafter referred to as a preoperative blood vessel pattern image), and an image representing a blood vessel pattern of the brain surface photographed by the microscope unit 110 during surgery (hereinafter referred to as an intraoperative blood vessel pattern image).

Figure 3:
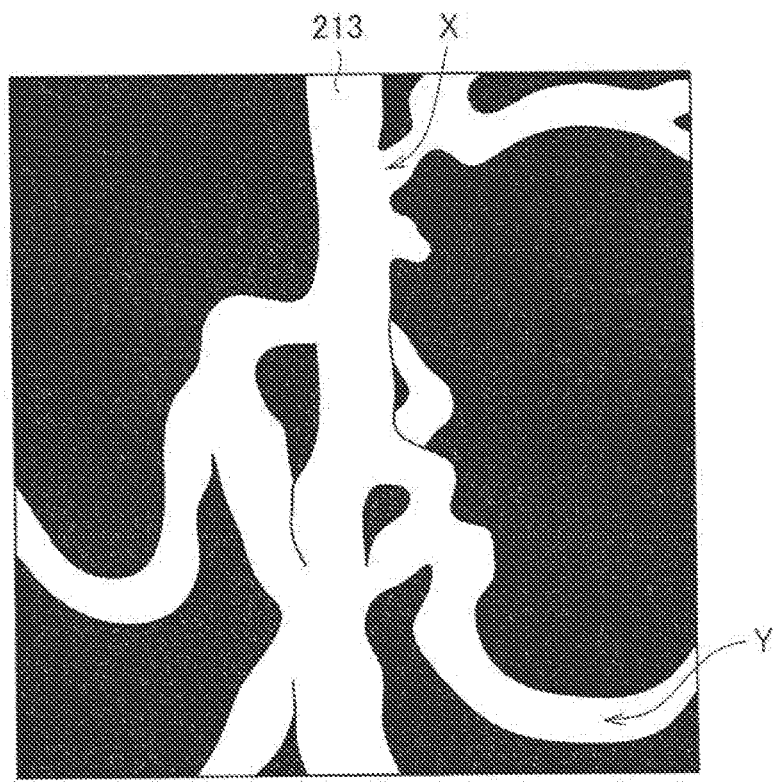
FIG. 3 is a diagram which shows an example of a preoperative blood vessel pattern image.

Specifically, the matching unit 142 first specifies a photographing direction of the microscope unit 110 and a craniotomy position on the basis of information regarding the three-dimensional positions of the head of the patient 201 and the microscope unit 110, which is provided from the position sensor 130. Next, the matching unit 142 extracts brain surface blood vessels from the 3D model of the brain generated by the 3D model generation unit 141, and generates a two-dimensional image in which the brain surface blood vessel is projected in the photographing direction of the microscope unit 110 at the specified craniotomy position, thereby generating a preoperative blood vessel pattern image. FIG. 3 is a diagram which shows an example of the preoperative blood vessel pattern image. As described above, this preoperative blood vessel pattern image can be clearly generated by using a blood vessel emphasis image as a diagnostic image for generating the 3D model of the brain.

Figure 4:
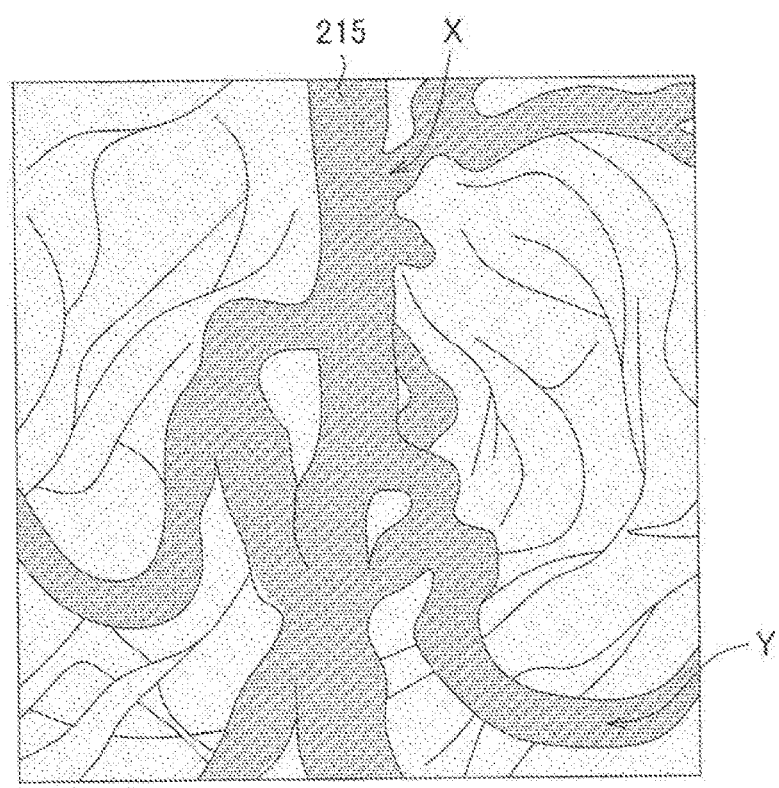
FIG. 4 is a diagram which shows an example of an intraoperative blood vessel pattern image.

Next, the matching unit 142, on the basis of information regarding a captured image provided from the microscope unit 110, extracts an image representing brain surface blood vessels in the open head, that is, an intraoperative blood vessel pattern image, from the captured image. FIG. 4 is a diagram which shows an example of the intraoperative blood vessel pattern image.

Then, the matching unit 142 performs matching processing between feature points of the generated preoperative blood vessel pattern image and intraoperative blood vessel pattern image. In the matching processing of feature points, for example, various types of known methods such as FAST, FASTX, STAR, SIFT, SURF, ORB, BRISK, MSER, GFTT, HARRIS, Dense, Simple Blob, and SmartAR (registered trademark) can be used. In these methods, it is possible to automatically obtain feature points (for example, as shown in FIGS. 3 and 4, a branch point X of blood vessels 213 and 215, a bending point Y of a blood vessel, and the like), and to evaluate a degree of matching between the two according to a degree of coincidence. At this time, since it is expected that there is blurring in distance and angle between the preoperative blood vessel pattern image and the intraoperative blood vessel pattern image due to brain shift, an affine transformation is performed on the preoperative blood vessel pattern image in a range with a minute magnification and a small angle to obtain a case in which a degree of coincidence is the highest in the changed range. As a result, brain surface blood vessels of a region (a photographing region) on the surface of brain exposed from the open head at the time of actual surgery and photographed by the microscope unit 110 are correlated with parts of the brain surface blood vessels of the 3D model generated by the 3D model generation unit 141. That is, a region on the surface of brain corresponding to the photographing region at the time of actual surgery is specified on the surface of the 3D model of the brain generated by the 3D model generation unit 141.

Here, since a reflection of light has a thin stripe shape in a case in which an elongated convex-shaped object is photographed like a blood vessel, in a blood vessel pattern image photographed by the microscope unit 110, a center of one blood vessel is not displayed, and the blood vessel may be recognized in a shape of being broken into two lines. In this case, synthesis processing in which these are regarded as one blood vessel can be generally performed by the image processing in processes of the various types of known matching processing. However, since the blood vessel has a curved complicated shape, and the reflection direction of the light is not uniform, the recognized stripe-shaped portion does not necessary take such a form as to border the blood vessel, and blood vessels which should originally have been connected may be recognized to be interrupted due to the synthesis processing described above. Therefore, in this case, a blood vessel pattern image in which border of the blood vessel is, so-called, in a dotted line shape can be obtained as the intraoperative blood vessel pattern image. In such a case, the matching unit 142 determines matching between an intraoperative blood vessel pattern image in a dotted line shape and a preoperative blood vessel pattern image in a solid line based on a vector direction and a disposition pattern of each image.

The matching unit 142 provides information regarding a matching result (that is, information regarding the specified region corresponding to the photographing region at the time of actual surgery on the surface of the 3D model of brain) to the brain shift amount estimation unit 143.

Note that, in the above description, as the intraoperative blood vessel pattern image, an image extracted from a captured image by the microscope unit 110, that is, an image with visible light, is used, but the present embodiment is not limited to such an example. As the intraoperative blood vessel pattern image, for example, an image photographed with an emphasis on blood vessels of indocyanine green (ICG) fluorescence blood angiography or the like. In this case, the microscope unit 110 includes a function of performing fluorescence photographing and ICG fluorescence images of blood vessels can be acquired by the microscope unit 110. It is possible to make a feature point in the intraoperative blood vessel pattern image clearer, and to cause accuracy of the matching processing to be improved by using such an image photographed with an emphasis on blood vessels.

Figure 5:
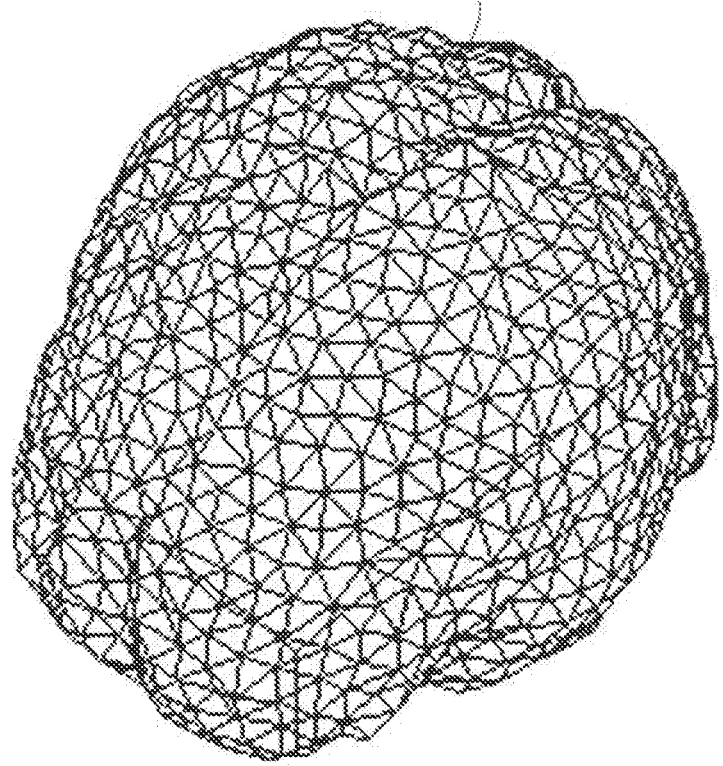
FIG. 5 is a diagram which shows an example of a calculation model of FEM.

The brain shift amount estimation unit 143 estimates an amount of deformation of brain caused by craniotomy from a preoperative state on the basis of a result of the matching processing by the matching unit 142. In the present embodiment, the brain shift amount estimation unit 143 estimates the amount of deformation of brain using a finite element method (FEM). Specifically, the brain shift amount estimation unit 143, first, generates a calculation model of the FEM by defining a three-dimensional mesh at each vertex of voxel of the 3D model of brain generated by the 3D model generation unit 141. FIG. 5 is a diagram which shows an example of a calculation model of the FEM. In the example shown in FIG. 5, a calculation model 217 of the FEM is generated by setting a mesh 219 in a regular tetrahedral shape with respect to the 3D model of brain.

Next, the brain shift amount estimation unit 143 sets an initial condition and a boundary condition for the FEM calculation. First, initial condition will be described. Specifically, the brain shift amount estimation unit 143 sets an amount of displacement of brain in the open head before surgery on the basis of a result of the matching processing by the matching unit 142 as the initial condition.

In the processing of setting the amount of displacement, the brain shift amount estimation unit 143 calculates three-dimensional coordinates in accordance with a current body position of the patient 201 in a region corresponding to a photographing region on the surface of the 3D model of brain in a case in which it is assumed that brain is not deformed are calculated on the basis of a result of the matching processing and information regarding a three-dimensional position of the head of the patient 201 provided from the position sensor 130. The three-dimensional coordinates are, that is, three-dimensional coordinates of each mesh of the region corresponding to the photographing region on a surface of the calculation model 217 in a case in which it is assumed that brain is not deformed.

On the other hand, the brain shift amount estimation unit 143 calculates actual three-dimensional coordinates of the surface of the brain in the photographing region on the basis of information regarding the three-dimensional positions of the head of the patient 201 and the microscope unit 110, which is provided from the position sensor 130, and depth information included in information regarding a captured image provided from the microscope unit 110.

A difference of these three-dimensional coordinates is the amount of displacement of brain in the photographing region, that is, the amount of displacement of brain in the open head. Since the brain shift amount estimation unit 143 obtains the amount of displacement of brain in the open head by calculating the difference, and sets a state in which a mesh of a position corresponding to the open head of the calculation model 217 is moved by the amount of displacement as the initial condition of the FEM calculation.

Figure 6:
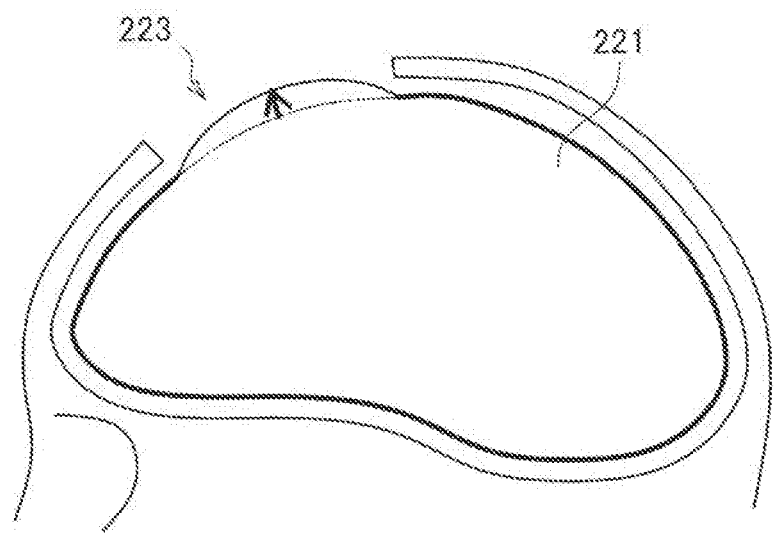
FIG. 6 is a diagram for describing swelling of a brain.
Figure 7:
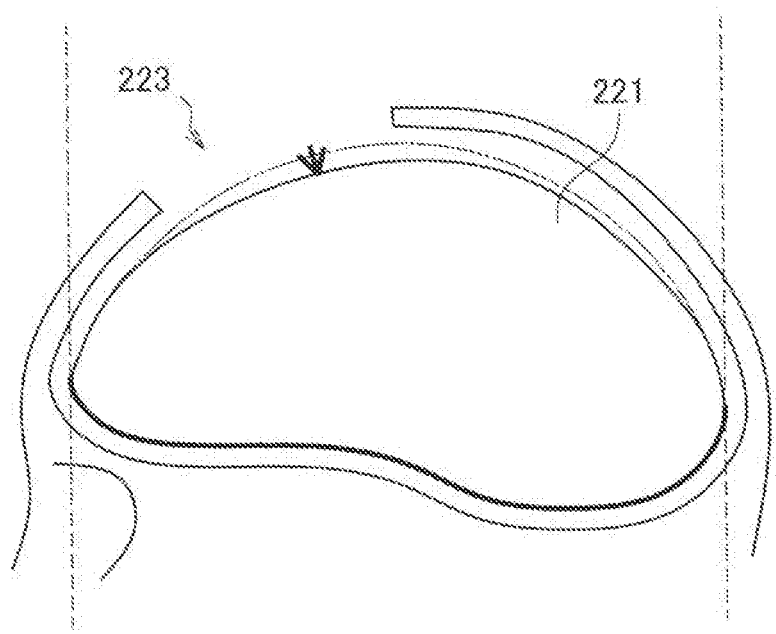
FIG. 7 is a diagram for describing subsidence of a brain.

Here, it is generally known that there are two types of brain shift at the time of craniotomy. They are brain swelling which can occur in an early stage of craniotomy and brain subsidence which can occur after an elapse of 10 minutes or more since the craniotomy. FIG. 6 is a diagram for describing brain swelling. FIG. 7 is a diagram for describing brain subsidence. FIGS. 6 and 7 schematically show a cross-section of the brain 221 at the middle.

In a case in which swelling occurs as shown in FIG. 6, the brain shift amount estimation unit 143 expresses a displacement of a mesh positioned at an open head 223 among meshes positioned on the surface of the calculation model 217 by extending a distance between respective points in these meshes. On the other hand, in a case in which subsidence occurs as shown in FIG. 7, the brain shift amount estimation unit 143 expresses a displacement of the mesh positioned at the open head 223 among the meshes positioned on the surface of the calculation model 217 by reducing a distance between respective points in these meshes.

Next, a boundary condition will be described. The brain shift amount estimation unit 143 sets a mesh which is in contact with cranial bone, dura, or the like and cannot physically move from an anatomical point of view as a fixed point with respect to the calculation model 217 as a boundary condition. A specific content of the boundary condition differs depending on an aspect (swelling or subsidence) of brain shift described above.

In a case in which swelling occurs as shown in FIG. 6, a region other than the open head 223 in the brain 221 is fixed by the cranial bone and the dura, and it is considered that a displacement due to the swelling converges on the open head 223. Therefore, in this case, the brain shift amount estimation unit 143 sets a mesh positioned in a region other than the open head 223 among the meshes positioned on the surface of the calculation model 217 as a fixed point which is not deformed as the boundary condition. In FIG. 6, a region corresponding to a mesh treated as a fixed point on the surface of the brain 221 is indicated by a bold line in a simulative manner.

On the other hand, in a case in which subsidence occurs as shown in FIG. 7, it is considered that a region below a contact point between an outer peripheral surface of the brain 221 and a vertical plane (shown by a dotted line in FIG. 7 in a simulative manner) showing a vertical direction which is a direction in which gravity acts is fixed by the cranial bone, and a region above it is displaced. Therefore, in this case, the brain shift amount estimation unit 143 sets a mesh positioned below the contact with the vertical plane among the meshes positioned on the surface of the calculation model 217 as a fixed point which is not deformed. In FIG. 7, in the same manner as in FIG. 6, a region corresponding to a mesh treated as a fixed point on the surface of the brain 221 is indicated as a bold line in a simulative manner.

Figure 8:
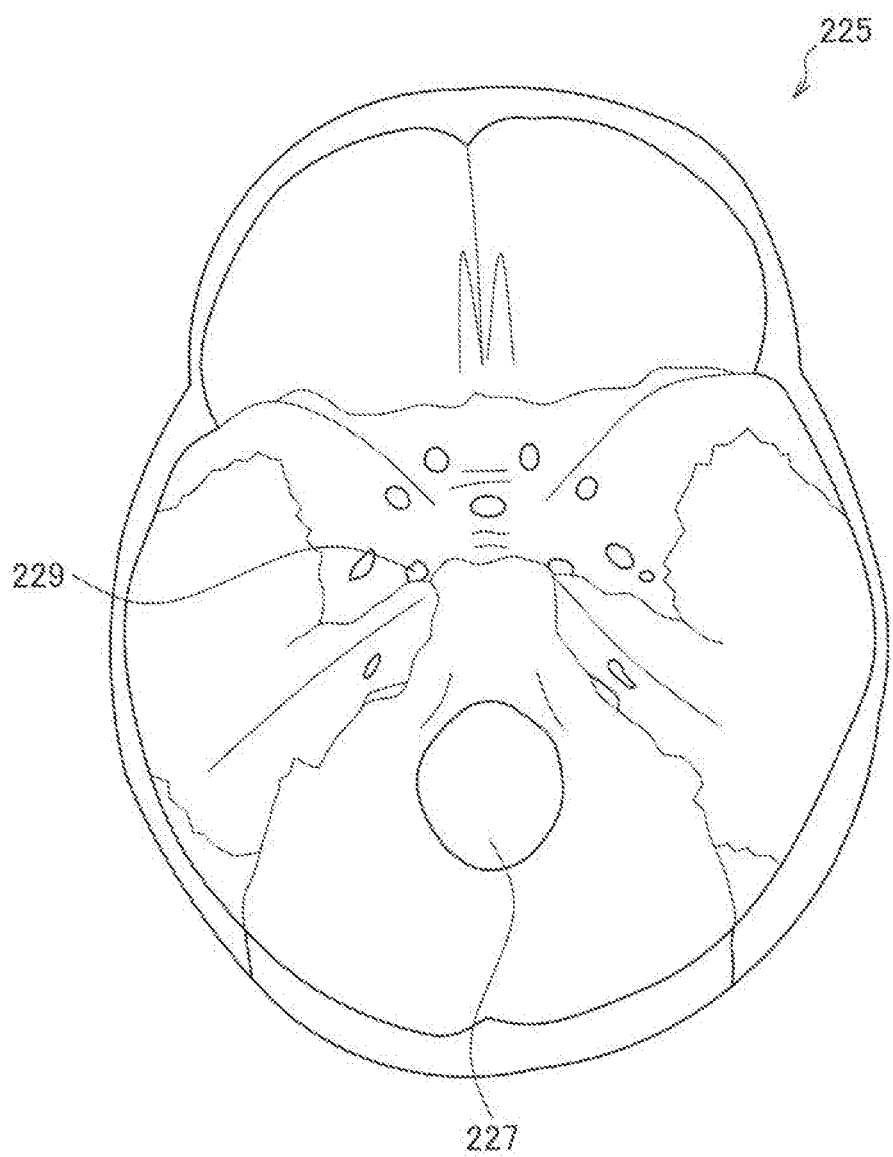
FIG. 8 is a diagram which schematically shows a state of a human skull base.

Alternatively, in a case in which subsidence occurs, another fixed point may also be set in consideration of a relationship between the brain 221 and a surrounding biological tissue (for example, spinal cords, blood vessel, nerves, and the like). Specifically, as shown in FIG. 8, large or small holes through which spinal cords, nerves, blood vessels, and the like pass are present in a human skull base. FIG. 8 is a diagram which schematically shows a state of the human skull base. FIG. 8 schematically shows a state in which a cranial cavity of human is horizontally cut and the human skull base is viewed from the above. A top of the page corresponds to the front.

As shown in FIG. 8, for example, a large occipital hole 227 through which spinal cords pass, a burst hole 229 through which carotid arteries pass, and the like are present in a skull base 225. Since these spinal cords and carotid arteries are joined to surrounding brain tissues by connective tissues, a part of the brain 221 which is joined to spinal cords and the like can be regarded as a fixed point which is not deformed. Accordingly, the brain shift amount estimation unit 143 may also set, in addition to the mesh positioned below the contact with the vertical plane, a mesh positioned at a place which is opposed to a hole through which spinal cords or the like are inserted and is assumed to be joined to the spinal cords and the like among meshes constituting the calculation model 217, and a mesh positioned between these meshes as fixed points which are not deformed.

Figure 9:
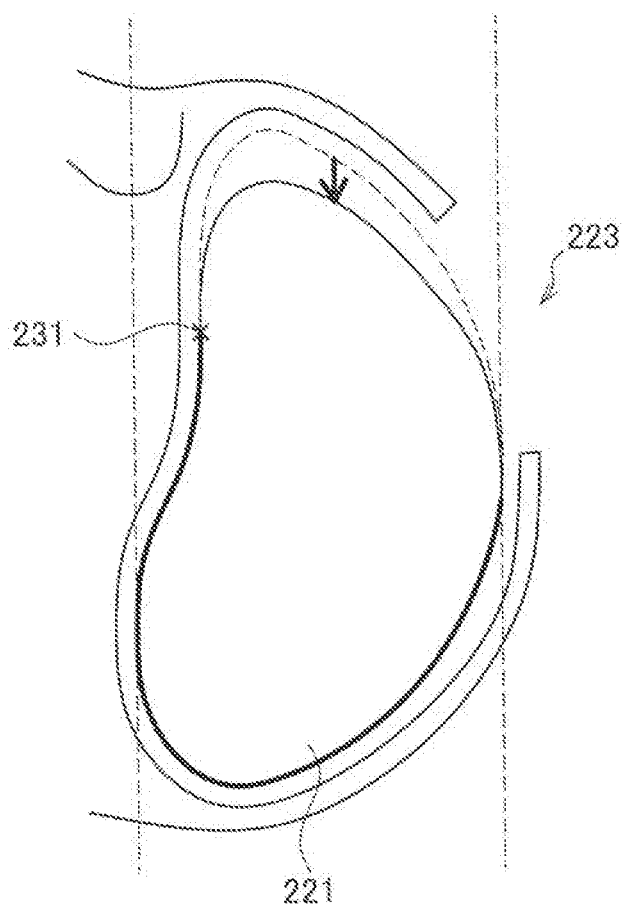
FIG. 9 is a diagram for describing, in a case in which subsidence of a brain occurs, a case in which a fixed point is set in consideration of a relationship between the brain and the spinal cord.

FIG. 9 is a diagram for explaining a case in which a fixed point is set even in consideration of a relation between the brain 221 and the spinal cords, and the like in the case in which subsidence of the brain 221 occurs. FIG. 9 schematically shows a cross section of the brain 221 taken along midline similarly to FIGS. 6 and 7. In addition, in FIG. 9, similarly to FIGS. 6 and 7, a region corresponding to the meshes treated as fixed points on the surface of the brain 221 are indicated by a bold line in a simulative manner.

In the example shown in FIG. 9, similarly to the case shown in FIG. 7, a mesh positioned below a contact point between the outer peripheral surface of the brain 221 and a vertical plane (shown by a dotted line in FIG. 9 in a simulative manner) is treated as a fixed point which does not deform. In the shown example, furthermore, a fixed point 231 which is a point fixed by being connected with a spinal cord, and the like on the surface of the brain 221 is added in consideration of a shape of the skull base 225 as described above. Then, a mesh positioned between the fixed point 231 and the contact point between the outer peripheral surface of the brain 221 and the vertical plane on the surface of the brain 221 is treated as a fixed point. In this manner, it is possible to set a boundary condition more suitable for an actual situation by setting a fixed point from an anatomical point of view in consideration of a shape of the cranial bone.

After setting the initial condition and the boundary condition, the brain shift amount estimation unit 143 calculates an amount of deformation of the entire calculation model 217, that is, an amount of brain shift, by an FEM. In such an FEM calculation, for example, brain 221 is treated as an elastic body and the amount of deformation of the calculation model 217 is calculated under the initial condition and boundary condition described above by using a stress-strain relational expression for an elastic body. For a ratio of Young's modulus to Poisson, physical property values of the brain 221 obtained from various types of literatures, and the like may be used. Since the FEM calculation can be performed by various known methods, a description of specific processing in the FEM calculation will be omitted.

Here, the brain shift amount estimation unit 143 calculates an amount of three-dimensional movement of a brain surface blood vessel in the open head 223 on the basis of a result of the matching processing by the matching unit 142 and the information regarding three-dimensional positions of the head of the patient 201 and the microscope unit 110 which are provided from the position sensor 130. Then, a shape of the deformed calculation model 217 is obtained such that a difference between the calculated amount of three-dimensional movement of a brain surface blood vessel in the calculated open head 223 and an amount of movement of a mesh positioned at the open head 223 is a minimum in the FEM calculation. The amount of displacement of each mesh 219 of the calculation model 217 in this state is the amount of movement of each voxel of the 3D model of the brain 221, that is, the amount of brain shift of the brain 221.

The brain shift amount estimation unit 143 provides information regarding the obtained amount of brain shift, that is, the amount of movement of each voxel of the 3D model of the brain 221, to the 3D model update unit 144.

The 3D model update unit 144 updates the 3D model of the brain 221 generated by the 3D model generation unit 141 on the basis of the information regarding the amount of brain shift obtained by the brain shift amount estimation unit 143. More specifically, the 3D model update unit 144 causes the 3D model to be deformed by moving each voxel of the 3D model of the brain 221 by an amount corresponding to the amount of brain shift obtained by the brain shift amount estimation unit 143. As a result, a 3D model which reflects the brain shift and in which an actual state of the brain 221 of the current patient 201 is more accurately represented is generated.

The 3D model update unit 144 provides information regarding the updated 3D model of the brain 221 to the display control unit 145.

The display control unit 145 controls driving of the display device 120 and causes the display device 120 to display a captured image of an operating site by the microscope unit 110. In addition, the display control unit 145 controls the driving of the display device 120, and causes the display device 120 to display a navigation image in which a display indicating a position of the treatment tool 205 is added to the 3D model of the brain 221 updated by the 3D model update unit 144. Note that, as described above, the captured image and the navigation image may be displayed on the same display device 120 or may be displayed on different display devices 120, respectively.

Here, "the display indicating the position of the treatment tool 205" may be an icon indicating the treatment tool 205 or a real image of the treatment tool 205 photographed by the microscope unit 110. The navigation image may be obtained by combining an icon indicating the treatment tool 205 with the 3D model of the brain 221, or superimposing a real image of the treatment tool 205 on the 3D model of the brain 221. In addition, in the navigation image, a lesion which is the operating site may be displayed in an emphasized manner, or a blood vessel or the like which is a dangerous part to avoid a contact with the treatment tool may be displayed in the emphasized manner. The emphasis display is performed, for example, by superimposing and displaying annotation information (including symbols, words, and/or images) in an operating site or a dangerous part. For example, the annotation information is given in advance to the 3D model of the brain 221 generated before surgery, and in this emphasis display, the annotation information reflects the amount of brain shift obtained by the brain shift amount estimation unit 143, and is given to a corresponding part of the 3D model of the brain 221 which is updated by the 3D model update unit 144. As a specific display mode of a navigation image, various modes used for a navigation image in a general surgical navigation system can be applied.

Figure 10:
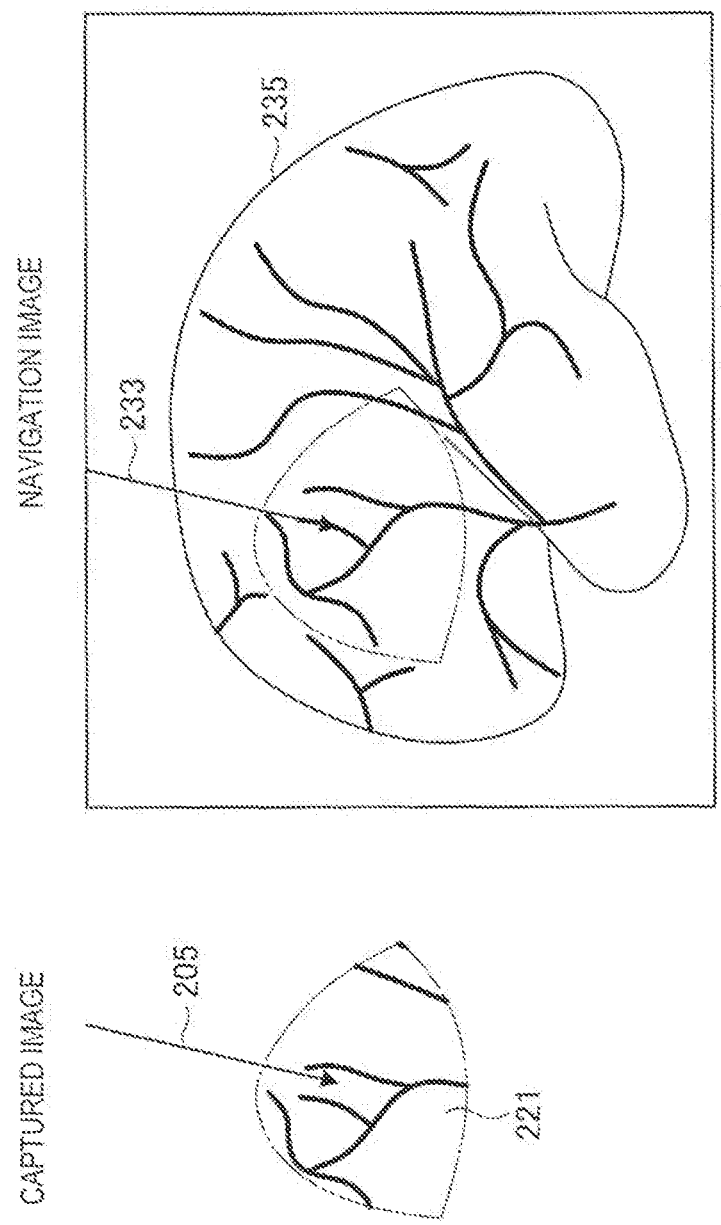
FIG. 10 is a diagram which schematically shows an example of a general existing navigation image in a brain surgical operation.
Figure 11:
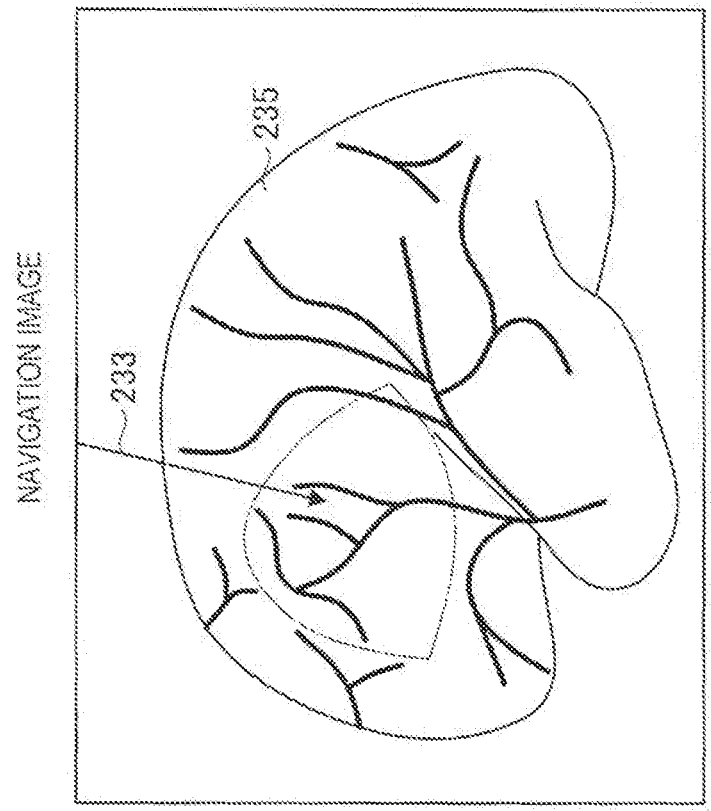
FIG. 11 is a diagram which schematically shows an example of a navigation image according to the present embodiment in a brain surgical operation.
Figure 11:
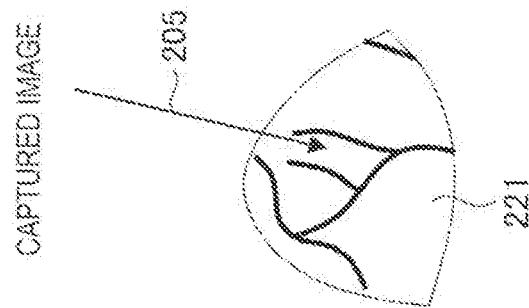

Here, FIG. 10 is a diagram schematically showing an example of a general existing navigation image in a brain surgical operation. FIG. 11 is a diagram schematically showing an example of a navigation image according to the present embodiment in a brain surgical operation. In FIGS. 10 and 11, a photographic image photographed by the microscope unit is shown by on the left side, and the navigation image is shown on the right side. As shown in FIG. 10, in the existing navigation image, since the 3D model of the brain 221 generated on the basis of a diagnostic image acquired before surgery is used as the navigation image as it is, deviation occurs by the amount of brain shift, a positional relationship between the actual treatment tool 205 and the blood vessels of the brain 221, and a positional relationship between an icon 233 indicating the treatment tool 205 in the navigation image and the blood vessels of the 3D model 235 of the brain 221.

On the other hand, as shown in FIG. 11, in a navigation image according to the present embodiment, since the 3D model of brain 221 generated before surgery is updated in accordance with the amount of brain shift and used for the navigation image, the positional relationship between the treatment tool 205 and the blood vessels of the brain 221 coincides with the positional relationship between the icon 233 indicating the treatment tool 205 in a navigation image and the blood vessels of the 3D model 235 of the brain 221 well.

In this manner, according to the present embodiment, the amount of brain shift is estimated, and a navigation image is generated using the 3D model of the brain 221 updated in accordance with the estimated amount of brain shift. Since the navigation image reflects a state of the actual brain 221 of the patient 201 at the time of surgery, a positional relationship between each tissue of the brain 221 (for example, an operating site, blood vessel, or the like.) of the brain 221 and the treatment tool 205 will be displayed more accurately in the navigation image. Therefore, it is possible to provide more useful information to surgeon, which is helpful for surgery.

In addition, at this time, estimation of the amount of brain shift is performed on the basis of depth information included in a captured image on the surface of the brain 221 acquired by the microscope unit 110, and information regarding the three-dimensional positions of the head of the patient 201 detected by the position sensor 130, the treatment tool 205, and the microscope unit 110. Performance of surgery while the brain 221 is photographed by the microscope unit 110 is generally performed in a brain surgical operation, and detection of the three-dimensional positions of the head of the patient 201 and the like by the position sensor 130 is widely used in an existing surgical navigation system. That is, according to the present embodiment, it is possible to estimate the amount of brain shift using existing facilities without newly adding a device or the like. Therefore, it is possible to obtain a more appropriate navigation image more easily.

Moreover, the amount of displacement of the three-dimensional position on the brain surface in the open head 223 is set as an initial condition at the time of calculating the amount of brain shift by performing the matching processing of blood vessel pattern images in the present embodiment. Here, for example, the amount of brain shift cannot be obtained with high accuracy only by measuring the amount of displacement of a certain point on the brain surface in the open head 223. In the present embodiment, using a result of the matching processing of blood vessel pattern images, the amount of displacement on the brain surface as a "surface" in the open head 223 is obtained, and the amount of brain shift is estimated using the amount of displacement, and thereby it is possible to obtain the amount of brain shift more accurately. Therefore, a more accurate navigation image which reflects an actual deformation of the brain 221 better is obtained.

Note that the amount of brain shift can change over time during surgery. Therefore, in the present embodiment, a series of processing after the matching processing of blood vessel pattern images described above are repeatedly executed at a predetermined interval (for example, 90 minutes, or the like) during surgery. As a result, since a navigation image conforming to a current situation is always displayed, a more accurate navigation image can be obtained.

Here, in a case in which the accuracy in the estimation of the amount of brain shift is lowered, a positional relationship between each tissue of the brain 221 and the treatment tool 205 is not accurately reflected in a navigation image using the 3D model of the brain 221 which is updated in accordance with the amount of brain shift. Performing surgery using such an inaccurate navigation image needs to be avoided from a safety point of view. Therefore, in the present embodiment, in a case in which it is concerned that the accuracy in the estimation of the amount of brain shift is low and an appropriate navigation image cannot be obtained, a function for issuing a warning is provided in the surgical navigation system 10.

More specifically, the image processing device 140 further includes a warning control unit 146 as its function. The warning control unit 146 controls driving of the display device 120 and/or other output devices (not shown), and issues a warning indicating that an appropriate navigation image cannot be obtained. In addition, in a case in which a navigation image is already displayed on the display device 120, the warning control unit 146 cancels the display of the navigation image together with a warning (that is, causes the navigation function to be stopped). The specific mode of the warning is not limited, and the warning may be, for example, a visual and/or audible warning. For example, the warning control unit 146 performs a warning by causing characters or the like to be displayed on the display device 120. Moreover, for example, the output device may be a bell or a speaker, and the warning control unit 146 performs a warning by voice via the bell or speaker.

Processing of determining whether or not an appropriate navigation image is obtained may be performed by matching unit 142. The matching unit 142 calculates a matching error when performing the matching processing as described above. Then, by comparing the matching error with a predetermined threshold value, it is determined whether an appropriate navigation image can be obtained. If the matching error is larger than the predetermined threshold value, matching processing is not appropriately performed, and the accuracy in estimation of the amount of brain shift performed on the basis of a result of the matching processing is highly likely to decrease. Therefore, in this case, the matching unit 142 determines that an appropriate navigation image cannot be obtained. On the other hand, if the matching error is equal to or smaller than the predetermined threshold value, matching processing is appropriately performed, and the accuracy in estimation of the amount of brain shift performed on the basis of a result of the matching processing is highly likely to be reliable. Therefore, in this case, the matching unit 142 determines that an appropriate navigation image can be obtained.

Specifically, an amount of three-dimensional movement before and after the craniotomy of brain surface blood vessels used for matching (that is, an amount of movement of the brain surface before and after the craniotomy in the open head 223) is used as the matching error in the present embodiment. That is, the matching unit 142 performs matching processing, and calculates the amount of three-dimensional movement of the brain surface blood vessel in the open head 223 on the basis of a result of the matching processing and the information regarding the three-dimensional positions of the head of the patient 201 and the microscope unit 110 provided from the position sensor 130. Here, it is generally said that the amount of brain shift is about 2 to 3 cm. Therefore, the matching unit 142 uses this general amount of brain shift as a threshold value and compares the amount of three-dimensional movement of a brain surface blood vessel in the open head 223 with the threshold value, thereby performing the determination processing described above.

Note that a matching error is not limited to the example, and the matching error may be calculated according to various evaluation functions used as an index indicating an error in matching processing of general images. In addition, a threshold value for determining whether the matching processing is appropriately performed may also be appropriately set in accordance with a type of the matching error.

In a case in which it is determined that an appropriate navigation image is not obtained as a result of the determination processing, the matching unit 142 provides information of the determination to the warning control unit 146. The warning control unit 146 which has acquired the information executes processing of causing the warning described above to be output.

Here, two factors are considered as factors for which the matching processing of blood vessel pattern images is not appropriately performed in the following description. The first factor is a shortage of blood vessel information during surgery. If defect information is insufficient, it is difficult to extract feature points, and there is a concern that matching processing between other parts having similar feature points can be performed. In addition, the second factor is deficiency of the brain 221 and large deformation associated with the progress of treatment.

Therefore, in the surgical navigation system 10, in a case in which a warning is issued, a message that blood vessel information needs to be newly acquired may be issued at the same time as the warning. In response to the message, to complement the blood vessel information, a diagnostic image of the patient 201 is newly acquired during surgery. Then, the 3D model generation unit 141 generates the 3D model of the brain 221 again on the basis of this diagnostic image newly acquired. Using this 3D model of the brain 221 newly generated, the matching processing of blood vessel pattern images by the matching unit 142 is performed, and the processing of determining whether or not an appropriate navigation image described above can be obtained is performed again. If a result of the determination is good, processing of estimating the amount of brain shift by the brain shift amount estimation unit 143 and processing of updating the 3D model by the 3D model update unit 144 are performed, and a navigation image using this updated 3D model can be displayed. In this manner, a safer surgery can be realized by displaying the navigation image only in a case in which it is determined that the appropriate navigation image can be obtained.

Note that a diagnostic image of patient 201 during surgery can be obtained by intraoperative MRA photography and/or intraoperative ICG fluorescence blood angiography and the like. In particular, in a case in which intraoperative ICG fluorescence blood angiography is used, photographing can be performed without causing the patient 201 on a patient bed to move, and thus it is convenient. Alternatively, in a case in which the matching processing of blood vessel pattern images is difficult, an angiographic X-ray image is imaged, and matching processing between a preoperative blood vessel pattern image and an intraoperative blood vessel pattern image may also be performed via the angiographic X-ray image such that matching processing between the intraoperative blood vessel pattern image and the angiographic X-ray image and matching processing between the angiographic X-ray imaging image and the preoperative blood vessel pattern image (for example, an image obtained by MRI, CT, or the like) are performed respectively. Here, angiographic X-ray photography is a photographing method which is widely used for observation of blood vessels and blood flows. In the angiographic X-ray photography, firstly, a contrast agent is intravenously injected into the patient 201. At this time, if X-ray video observation is performed, it is possible to observe a state in which light is gradually bright in order of heart, artery, peripheral, and vein. Here, in the angiographic X-ray photography, a target part of the patient 201 is photographed by an X-ray CT device. As a result, it is possible to obtain information regarding such as a three-dimensional position of a blood vessel, a blood vessel branch level, a blood flow direction, blood retention, and the like.

The configuration of the surgical navigation system 10 according to the present embodiment has been described above. As described above, according to the present embodiment, since a more accurate disease position can be displayed in a navigation image in accordance with the brain shift, this can help a surgeon to do an exact procedure. Furthermore, surgery mistakes can be prevented and further safety can be secured by evaluating appropriateness of the navigation image, and urging a navigation stop or 3D model update in accordance with a result of the evaluation.

Note that, a target on which the matching unit 142 performs the matching processing is a two-dimensional image in the above description, but the present embodiment is not limited to this example. For example, the matching unit 142 may perform the matching processing between a 3D model of a brain surface blood vessel extracted from the 3D model of the brain 221 and a 3D model of a brain surface blood vessel extracted using the depth information from a captured image by the microscope unit 110.

Also, in the above description, the display control unit 145 causes the one or more display devices 120 to display a captured image of the operating site photographed during surgery by the microscope unit 110 and a navigation image. At this time, annotation information (including symbols, words and/or images) may also be displayed to be superimposed on the captured image. For example, in the 3D model of brain obtained before surgery, annotation information given to a part to be displayed in an emphasized manner such as an operating site and a dangerous part is superimposed to a part corresponding to a captured image photographed during surgery as an image of a frame surrounding the part or the like. At this time, on the basis of the amount of brain shift obtained by the brain shift amount estimation unit 143, in a case in which the part to be displayed in the emphasized manner in the captured image during surgery moves, the annotation information set before surgery is not displayed as it is, but may be displayed appropriately in accordance with a display form and state of the corresponding part in the captured image during surgery, such as causing the movement to be followed by a display of the annotation information. In addition, the annotation information may include a voice, and, for example, in a case in which the treatment tool 205 approaches a predetermined region (for example, a region where attention is desired to be called) in the navigation image, voices for calling attention to the effect may also be issued via an output device (not shown).

In the above description, in a case in which the matching error in the matching processing by the matching unit 142 is large, a warning for the fact is issued and a message indicating that new blood vessel information needs be acquired (that is, a message to the effect that a diagnostic image needs to be acquired again) has been issued, but this embodiment is not limited to such an example. For example, instead of or in combination with these pieces of processing, a numerical value serving as an index indicating a degree of the matching error, a numerical value serving as an index indicating a reliability of the matching processing which can be appropriately calculated from the matching error, or the like may be displayed on the display device 120 under the control from the warning control unit 146. By performing such a display, a surgeon can ascertain an accuracy of the matching error quantitatively, and thus it is possible to appropriately determine whether a diagnostic image needs to be acquired again, for example, in accordance with a surgical procedure or the like. Therefore, in a case in which a surgeon determines that the matching error is not that large and surgery can be performed safely without necessarily acquiring a diagnostic image again, surgery can continue as it is, and thus smoother surgery can be realized.

Alternatively, instead of or in addition to the processing of issuing a warning to the effect that the matching error is large and the processing of issuing a message to the effect that new blood vessel information needs to be obtained, other warnings based on the matching error may be displayed on the display device 120 under the control from the warning control unit 146. For example, in a case in which regions where the matching error occurs are concentrated in a specified part in an image, there is a concern that lesions accompanied by blood vessel rupture, risk of ischemia, and the like may occur at the part. Accordingly, in such a case, a frame enclosing the corresponding part may be displayed, and a word notifying that a risk is likely to increase in the part may be displayed in a navigation image on the display device 120 or a captured image photographed by the microscope unit 110.

Note that a specific device configuration of the image processing device 140 is not limited. The image processing device 140 may be configured to realize the above-described functions, and the specific device configuration may be arbitrary. For example, the image processing device 140 may be constituted by one device or may be constituted by a plurality of devices. In the case in which the image processing device 140 constituted by a plurality of devices, for example, if the functions schematically shown by the blocks in FIG. 1 are distributed and mounted in the plurality of devices and the plurality of devices are connected to communicate with each other to operate in cooperation with each other, functions similar to those of the image processing device 140 can be realized.

In addition, a computer program for realizing each of the functions of the image processing device 140 illustrated in FIG. 1 can be produced can installed in a processing device such as a PC. In addition, a computer-readable recording medium storing such a computer program can also be provided. The recording medium is, for example, a magnetic disk, an optical disc, a magneto-optical disc, a flash memory, or the like. In addition, the computer program may be distributed via, for example, a network, without using a recording medium.

3. Image Processing Method

Figure 12:
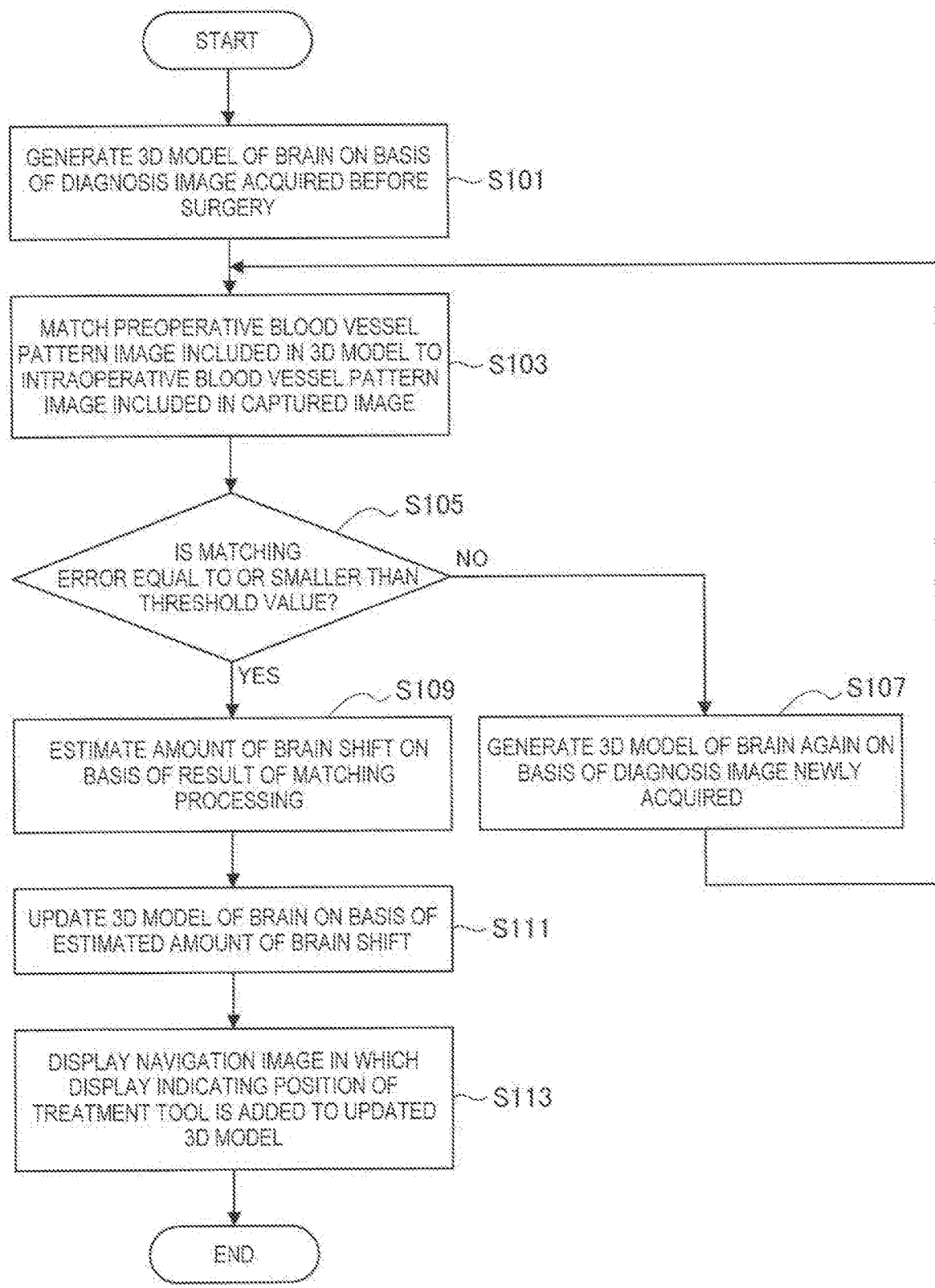
FIG. 12 is a flowchart which shows an example of a processing procedure of an image processing method according to the present embodiment.

A processing procedure of an image processing method according to the present embodiment will be described with reference to FIG. 12. FIG. 12 is a flowchart illustrating an example of the processing procedure of the image processing method according to the present embodiment. Note that each of the processes shown in FIG. 12 corresponds to the processes executed by the image processing device 140 of the surgical navigation system 10 illustrated in FIG. 1. Since details of the processes have already been described in the description of the functional configuration of the surgical navigation system 10, detailed description of each process will be omitted in the following description of the processing procedure of the image processing method.

Referring to FIG. 12, a 3D model of brain is first generated on the basis of a diagnostic image acquired before surgery (step S101) in the image processing method according to the present embodiment. The processing shown in step S101 corresponds to the processing executed by the 3D model generation unit 141 of the image processing device 140 shown in FIG. 1.

Note that the processing shown in step S101 described above can be executed before surgery is started. After the processing shown in step S101 is performed, setting of the surgery is performed. The setting of the surgery may specifically be carrying into a surgery room of the patient 201, craniotomy work for causing an operating site to be exposed, disposition of medical staff and surgery equipment, and the like. Then, processing of step S103 and the subsequent processing are processing executed during the surgery.

If the surgery is started, a preoperative blood vessel pattern image of the surface of brain included in the 3D model is next matched to an intraoperative blood vessel pattern image of the surface of brain included in a captured image photographed by the microscope unit 110 in the image processing method according to the present embodiment (step S103).

Next, it is determined whether the matching error is equal to or smaller than a threshold value (step S105). The processing shown in step S103 and step S105 corresponds to processing executed by the matching unit 142 of the image processing device 140 shown in FIG. 1.

In a case in which it is determined that the matching error is larger than the threshold value in step S105, matching between the preoperative blood vessel pattern image and the intraoperative blood vessel pattern image is not appropriately performed, and, as a result, estimation of the amount of brain shift is not performed with high accuracy, and it is considered that an appropriate navigation image cannot be obtained. In this case, a diagnostic image is newly acquired. Then, the 3D model of brain is generated again on the basis of the diagnostic image newly acquired (step S107). Then, the matching processing of a blood vessel pattern image is executed again by returning to step S103. Note that processing of displaying a numerical value serving as an index indicating a degree of the matching error, a numerical value serving as an index indicating a reliability of the matching processing, or the like may also be performed before the processing shown in step S107. In this case, the procedure may proceed to step S109 in a case in which it is determined that a surgeon performs matching processing with sufficient accuracy, the procedure may proceed to step S107 only in a case in which there is an instruction by the surgeon, and the 3D model of brain may be generated again on the basis of the diagnostic image newly generated.

On the other hand, in a case in which it is determined that the matching error is equal to or smaller than the threshold value in step S105, the procedure proceeds to step S109. In step S109, the amount of brain shift is estimated on the basis of a result of the matching processing of a blood vessel pattern image. The processing shown in step S109 corresponds to processing executed by the brain shift amount estimation unit 143 of the image processing device 140 shown in FIG. 1.

Next, the 3D model of brain is updated on the basis of the estimated amount of brain shift (step S111). The processing shown in step S111 corresponds to processing executed by the 3D model update unit 144 of the image processing device 140 shown in FIG. 1.

Then, a navigation image in which a display indicating a position of the treatment tool 205 is added to an updated 3D model is displayed on the display device 120 (step S113). The processing shown in step S113 corresponds to processing executed by the display control unit 145 of the image processing device 140 shown in FIG. 1.

As described above, the processing procedure of the image processing method according to the present embodiment has been described.

4. Configuration Example of Observation Device

Figure 13:
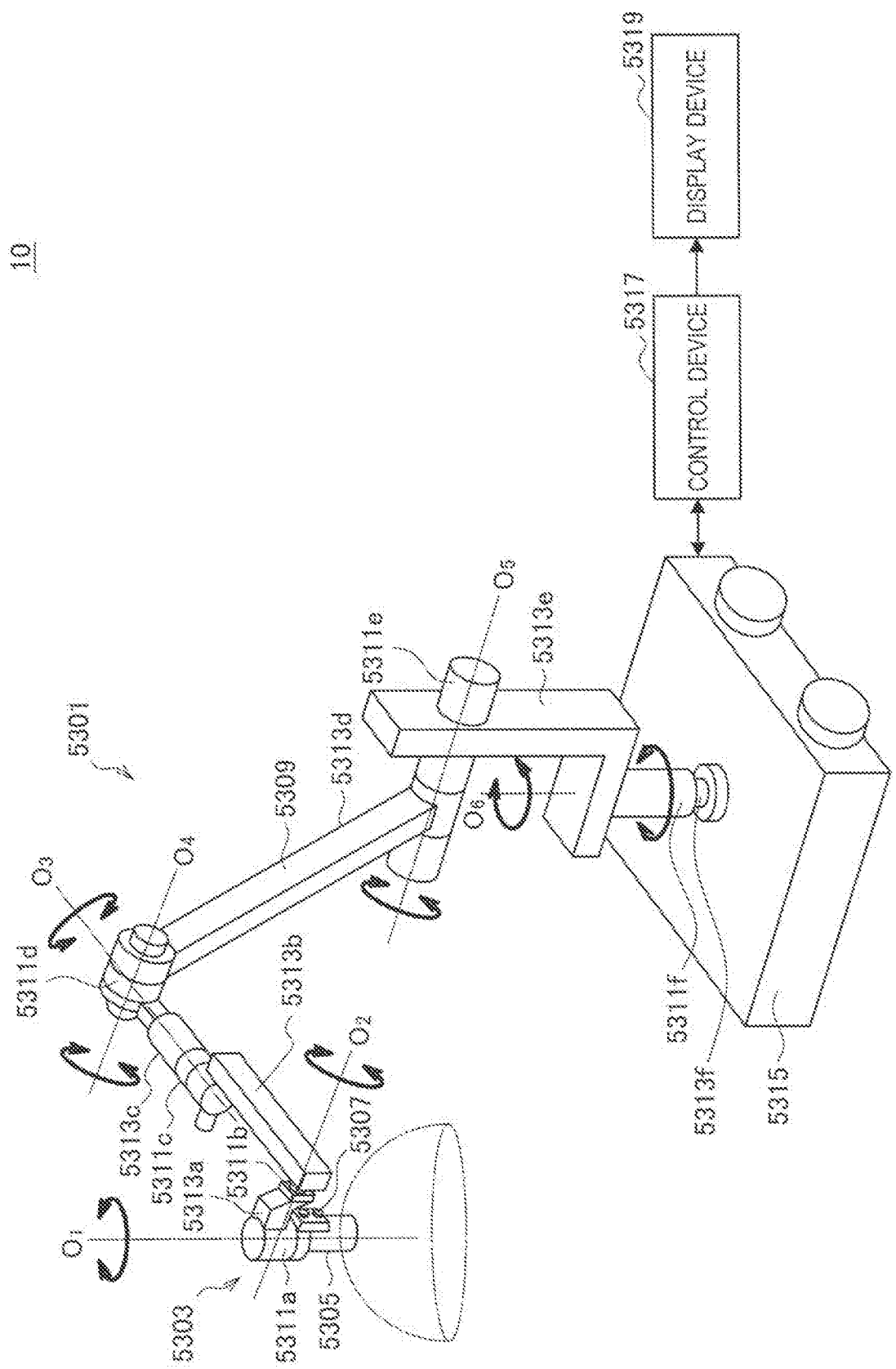
FIG. 13 is a diagram which shows a configuration of the surgical navigation system according to the present embodiment, including a detailed configuration of an observation device.

A specific configuration example of an observation device included in the microscope unit 110 described above will be described. FIG. 13 is a diagram which shows a configuration of the surgical navigation system 10 according to the present embodiment, including a detailed configuration of an observation device.

With reference to FIG. 13, the surgical navigation system 10 includes an observation device 5301, a control device 5317, and a display device 5319. Note that the display device 5319 corresponds to the display device 120 shown in FIG. 1 as described above, and thus description thereof will be omitted.

Referring to FIG. 8, the observation device 5301 has the microscope unit 5303 for enlarging and observe an observation target (an operating site of the patient 201), the arm unit 5309 supporting the microscope unit 5303 at its tip, a base unit 5315 supporting the base end of the arm unit 5309, and a control device 5317 that comprehensively control operations of the observation device 5301. The microscope unit 5303 corresponds to the microscope unit 110 shown in FIG. 1 as described above.

The microscope unit 5303 is made up of an approximately cylindrical barrel unit 5305, an imaging unit (not illustrated) provided inside the barrel unit 5305, and an operating unit 5307 provided in a partial region on the outer circumference of the barrel unit 5305.

The aperture on the bottom end of the barrel unit 5305 is provided with a cover glass that protects the imaging unit inside. Light from the observation target (hereinafter, also referred to as observation light) passes through the cover glass and is incident on the imaging unit inside the barrel unit 5305. Note that a light source made up of a light-emitting diode (LED) or the like, for example, may also be provided inside the barrel unit 5305, and during imaging, light may be radiated from the light source onto the observation target through the cover glass. In a case in which ICG fluorescence blood angiography is performed, the light source can be configured to emit excitation light of a predetermined wavelength corresponding to ICG The imaging unit is made up of an optical system that condenses observation light, and an image sensor that senses the observation light condensed by the optical system. The optical system is made up of a combination of multiple lenses, including a zoom lens and a focus lens, the optical characteristics of which are adjusted so that an image of the observation light is formed on the light-sensitive face of the image sensor. The image sensor senses and photoelectrically converts the observation light to thereby generate an image signal corresponding to the observed image. A sensor capable of color photography including a Bayer array, for example, is used as the image sensor. The image sensor may be any of various known types of image sensors, such as a complementary metal-oxide-semiconductor (CMOS) image sensor or a charge-coupled device (CCD) image sensor. The image signal generated by the image sensor is transmitted to the control device 5317 as RAW data. At this point, the transmission of the image signal may be conducted favorably by optical communication. This is because at the surgery venue, the surgeon performs surgery while observing the state of the affected area via the captured image, and thus for safer and more reliable surgery, there is demand for the moving image of the operating site to be displayed as close to real-time as possible. Transmitting the image signal by optical communication makes it possible to display the captured image with low latency.

Note that the imaging unit may also include a driving mechanism that moves the zoom lens and the focus lens of the optical system along the optical axis. By suitably moving the zoom lens and the focus lens with the driving mechanism, the magnification factor of the captured image and the focal distance during imaging may be adjusted. Also, the imaging unit may be provided with any of various types of functions typically provided in electronic imaging microscope units, such as an auto exposure (AE) function, an AF function or the like.

In addition, the imaging unit may be configured as a so-called single-plate imaging unit having one image sensor, and may also be configured as a so-called multi-plate imaging unit having a plurality of image sensors. In a case of the multi-plate imaging unit, for example, image signals corresponding to RGB by each image sensor are generated, and a color image may also be obtained by synthesizing these. Alternatively, the imaging unit may also be configured to have a pair of image sensors (that is, as a stereo camera) for acquiring image signals for a right eye and a left eye corresponding to stereoscopic viewing (a 3D display). With a 3D display being performed, a surgeon can more accurately ascertain a depth of a biological tissue in an operating site. Note that multiple systems of optical systems can be provided to correspond to each image sensor in a case of the multi-plate imaging unit.

The operating unit 5307 is constituted by, for example, a 4-direction lever, a switch, or the like, and is an input means that receives operation input of the surgeon. For example, the surgeon can input an instruction to change an enlargement magnification and a focal distance to an observation target of an observation image via the operating unit 5307. When the driving mechanism of the imaging unit appropriately moves the zoom lens and the focus lens in accordance with the instruction, the enlargement magnification and the focal distance can be adjusted. In addition, for example, the surgeon can input an instruction to further switch the operation mode of the arm unit 5309 (an all-free mode and a locked mode, which will be described below) via the operating unit 5307. Note that, in a case in which the surgeon attempts to move the microscope unit 5303 in the manual mode, an aspect in which the surgeon moves the microscope unit 5303, holding the barrel unit 5305 is assumed. Thus, it is preferable for the operating unit 5307 to be provided at a position at which the surgeon can easily operate the operating unit with his or her finger, holding the barrel unit 5305 so that the surgeon can operate it while moving the barrel unit 5305.

The arm unit 5309 is configured as a result of multiple links (a first link 5313a to a sixth link 5313f) being rotatably joined to each other by multiple joint units (a first joint unit 5311a to a sixth joint unit 5311f).

The first joint unit 5311a has an approximately cylindrical shape, and on the leading end (bottom end) thereof supports the top end of the barrel unit 5305 of the microscope unit 5303, so as to allow rotation about a rotation axis (first axis O1) parallel to the central axis of the barrel unit 5305. Herein, the first joint unit 5311a may be configured so that the first axis O1 is aligned with the optical axis of the imaging unit of the microscope unit 5303. Consequently, rotating the microscope unit 5303 about the first axis O1 makes it possible to change the field of view as though rotating the captured image.

The first link 5313a securely supports the first joint unit 5311a on the leading end thereof. Specifically, the first link 5313a is an approximately L-shaped rod-like member, the leading edge of which extends in a direction orthogonal to the first axis O1, while also being connected to the first joint unit 5311a so that the end of that edge abuts the top end on the outer circumference of the first joint unit 5311a. The second joint unit 5311b is connected to the end of the base edge of the approximate L-shape of the first link 5313a.

The second joint unit 5311b has an approximately cylindrical shape, and on the leading end thereof supports the base end of the first link 5313a, so as to allow rotation about a rotation axis (second axis O2) orthogonal to the first axis O1. The leading end of the second link 5313b is securely connected to the base end of the second joint unit 5311b.

The second link 5313b is an approximately L-shaped rod-like member, the leading edge of which extends in a direction orthogonal to the second axis O2, while the end of that edge is securely connected to the base end of the second joint unit 5311b. The third joint unit 5311c is connected to the base edge of the approximate L-shape of the second link 5313b.

The third joint unit 5311c has an approximately cylindrical shape, and on the leading end thereof supports the base end of the second link 5313b, so as to allow rotation about a rotation axis (third axis O3) orthogonal to both the first axis O1 and the second axis O2. The leading end of the third link 5313c is securely connected to the base end of the third joint unit 5311c. By rotating the configuration on the leading-end side, including the microscope unit 5303, about the second axis O2 and the third axis O3, the microscope unit 5303 may be moved to change the position of the microscope unit 5303 on the horizontal plane. In other words, controlling the rotation about the second axis O2 and the third axis O3 makes it possible to move the field of view of the captured image on a flat plane.

The third link 5313c is configured to have an approximately cylindrical shape on the leading end side, and on the leading end of the cylindrical shape, the base end of the third joint unit 5311c is securely connected so that both have approximately the same central axis. The base end side of the third link 5313c has a rectangular column shape, and the fourth joint unit 5311d is connected to the end thereof.

The fourth joint unit 5311d has an approximately cylindrical shape, and on the leading end thereof supports the base end of the third link 5313c, so as to allow rotation about a rotation axis (fourth axis O4) orthogonal to the third axis O3. The leading end of the fourth link 5313d is securely connected to the base end of the fourth joint unit 5311d.

The fourth link 5313d is a rod-like member that extends approximately linearly in a direction orthogonal to the fourth axis O4, while also being securely connected to the fourth joint unit 5311d so that the leading end abuts the side face of the approximately cylindrical shape of the fourth joint unit 5311d. The fifth joint unit 5311e is connected to the base end of the fourth link 5313d.

The fifth joint unit 5311e has an approximately cylindrical shape, and on the leading end side thereof supports the base end of the fourth link 5313d, so as to allow rotation about a rotation axis (fifth axis O5) parallel to the fourth axis O4. The leading end of the fifth link 5313e is securely connected to the base end of the fifth joint unit 5311e. The fourth axis O4 and the fifth axis O5 are rotation axes enabling the microscope unit 5303 to be moved in the vertical direction. By rotating the configuration on the leading-end side, including the microscope unit 5303, about the fourth axis O4 and the fifth axis O5, the height of the microscope unit 5303, or in other words the distance between the microscope unit 5303 and the observation target, may be adjusted.

The fifth link 5313e is made up of a combination of a first member having an approximate L-shape with one edge extending in the vertical direction while the other edge extends in the horizontal direction, and a rod-like second member that extends vertically downward from the unit of the first member that extends in the horizontal direction. The base end of the fifth joint unit 5311e is securely connected near the top end of the unit of the first member that extends in the vertical direction of the fifth link 5313e. The sixth joint unit 5311f is connected to the base end (bottom end) of the second member of the fifth link 5313e.

The sixth joint unit 5311f has an approximately cylindrical shape, and on the leading end side thereof supports the base end of the fifth link 5313e, so as to allow rotation about a rotation axis (sixth axis O6) parallel to the vertical direction. The leading end of the sixth link 5313f is securely connected to the base end of the sixth joint unit 5311f.

The sixth link 5313f is a rod-like member that extends in the vertical direction, with the base end securely connected to the top face of the base unit 5315.

The allowable rotation range of the first joint unit 5311a to the sixth joint unit 5311f is suitably set so that the microscope unit 5303 is capable of desired motion. Consequently, in the arm unit 5309 having the configuration described above, three degrees of translational freedom and three degrees of rotational freedom, for a total of six degrees of freedom, may be realized for the motion of the microscope unit 5303. In this way, by configuring the arm unit 5309 so that six degrees of freedom are realized for the motion of the microscope unit 5303, it becomes possible to freely control the position and the attitude of the microscope unit 5303 within the movable range of the arm unit 5309. Consequently, it becomes possible to observe an operating site from any angle, and surgery may be executed more smoothly.

Note that the configuration of the arm unit 5309 illustrated in the diagram is merely one example, and factors such as the number and the shapes (lengths) of the links constituting the arm unit 5309, as well as the number and arrangement of the joint units and the directions of the rotation axes may be designed suitably so that the desired degrees of freedom may be realized. For example, as described above, to move the microscope unit 5303 freely, the arm unit 5309 preferably is configured to have six degrees of freedom, but the arm unit 5309 may also be configured to have more degrees of freedom (in other words, redundant degrees of freedom). When redundant degrees of freedom exist, in the arm unit 5309, it becomes possible to change the attitude of the arm unit 5309 while keeping the position and the attitude of the microscope unit 5303 in a locked state. Accordingly, for example, control for higher convenience such as controlling the attitude of the arm unit 5309 such that the arm unit 5309 does not interfere with a view of a surgeon looking at the display device 5319 can be realized by the surgeon.

Herein, the first joint unit 5311a to the sixth joint unit 5311f may be provided with actuators equipped with a driving mechanism such as a motor, an encoder that detects the rotation angle in each joint unit, and the like. In addition, by having the control device 5317 suitable control the driving of each actuator provided for the first joint unit 5311a to the sixth joint unit 5311f, the attitude of the arm unit 5309, or in other words the position and the attitude of the microscope unit 5303, may be controlled. Specifically, the control device 5317 may ascertain the current attitude of the arm unit 5309 and the current position and attitude of the microscope unit 5303 on the basis of information regarding the rotation angle of each joint unit detected by the encoder. The control device 5317 calculates a control value (for example, a rotation angle, generated torque, or the like) for each joint unit to realize the movement of the microscope unit 5303 in accordance with an operation input from the surgeon using these pieces of ascertained information, and causes a drive mechanism of each joint unit to be driven in accordance with the control value. Note that, at that time, a control method of the arm unit 5309 by the control device 5317 is not limited, and various known control methods such as force control or position control may be applied.

For example, a surgeon appropriately performs an operation input via an input device (not shown), and thereby the driving of the arm unit 5309 may be appropriately controlled by the control device 5317 in accordance with the operation input, and the position and the attitude of the microscope unit 5303 may be controlled. With this control, after the microscope unit 5303 is caused to move from an arbitrary position to an arbitrary position, it can be fixedly supported at the position after the movement. Note that, as the input device, it is preferable to apply an operable device even if the surgeon has a treatment tool in his or her hand, such as a foot switch, considering the convenience of the surgeon. In addition, the operation input may be performed in a non-contact manner on the basis of gesture detection or sight line detection using a wearable device or a camera provided in a surgery room. As a result, a surgeon belonging to the clean area can also operate devices belonging to filthiness at a higher degree of freedom. Alternatively, the arm unit 5309 may be operated in a so-called master-slave manner. In this case, the arm unit 5309 may be remotely controlled by the surgeon via an input device installed at a location remote from a surgery room.

In a case in which the force control is applied, a so-called power assist control in which the actuators of the first joint unit 5311a to the sixth joint unit 5311f are driven so that the external force from the surgeon is received and the arm unit 5309 moves smoothly according to the external force may be performed. As a result, when the surgeon grasps the microscope unit 5303 and attempts to move the position directly, it is possible to move the microscope unit 5303 with a relatively light force. Therefore, it is possible to move the microscope unit 5303 more intuitively using a simpler operation, and to improve the convenience of the surgeon.

In addition, the driving of the arm unit 5309 may be controlled such that a pivoting operation is performed. Here, the pivoting operation is an operation of moving the microscope unit 5303 so that the optical axis of the microscope unit 5303 always faces a predetermined point on the space (hereinafter, referred to as a pivot point). According to the pivoting operation, it is possible to observe the same observation position from various directions, and thus more detailed observation of an affected area is possible. Note that, in a case in which the microscope unit 5303 is configured such that a focal distance thereof cannot be adjusted, it is preferable that a pivoting operation is performed in a state in which a distance between the microscope unit 5303 and the pivot point is in a locked state. In this case, the distance between the microscope unit 5303 and the pivot point may be adjusted to a fixed focal distance of the microscope unit 5303. As a result, the microscope unit 5303 moves on a hemisphere having a radius corresponding to the focal distance centered on the pivot point (schematically shown in FIG. 13), and even if the observation direction is changed, a clear captured image will be obtained. On the other hand, in a case in which the microscope unit 5303 is configured such that a focal distance thereof can be adjusted, a pivoting operation may be performed in a state in which the distance between the microscope unit 5303 and the pivot point is variable. In this case, for example, the control device 5317 may calculate the distance between the microscope unit 5303 and the pivot point on the basis of the information regarding the rotation angle of each joint unit detected by the encoder, and may adjust automatically the focal distance of the microscope unit 5303 on the basis of a result of the calculation. Alternatively, according to a case in which an AF function is provided in the microscope unit 5303, the focal distance adjustment may be automatically performed by the AF function every time the distance between the microscope unit 5303 and the pivot point changes due to the pivoting operation.

In addition, the first joint unit 5311a to the sixth joint unit 5311f may also be provided with brakes that restrain rotation. The operation of such brakes may be controlled by the control device 5317. For example, when it is desirable to lock the position and the attitude of the microscope unit 5303, the control device 5317 applies the brake on each joint unit. As a result, the attitude of the arm unit 5309, or in other words the position and the attitude of the microscope unit 5303, may be locked without driving the actuators, and power consumption may be reduced. When it is desirable to move the position and the attitude of the microscope unit 5303, it is sufficient for the control device 5317 to release the brake on each joint unit and drive the actuators according to a predetermined control scheme.

Such a brake operation input may be performed in response to operation performed by the surgeon via the operating unit 5307 described above. When the user wants to move the position and the attitude of the microscope unit 5303, the surgeon operates the operating unit 5307 to release the brake on each joint unit. As a result, the operation mode of the arm unit 5309 switches to a mode allowing each joint unit to be rotated freely (all-free mode). Meanwhile, when the surgeon wants to lock the position and the attitude of the microscope unit 5303, the user operates the operating unit 5307 to apply the brake on each joint unit. As a result, the operation mode of the arm unit 5309 switches to a mode in which the rotation of each joint unit is restrained (locked mode).

The control device 5317 generally controls an operation of the surgical navigation system 10 by controlling operations of the observation device 5301 and the display device 5319. For example, the control device 5317 controls driving of the arm unit 5309 by causing actuators of the first joint unit 5311a to the sixth joint unit 5311f to operate according to a predetermined control method. In addition, for example, the control device 5317 changes an operation mode of the arm unit 5309 by controlling brake operations of the first joint unit 5311a to the sixth joint unit 5311f.

Here, the control device 5317 may include a function of the image processing device 140 shown in FIG. 1 as described above. That is, the control device 5317 has a combination of a function of the image processing device 140 and each function related to driving of the observation device 5301 described above. Specifically, for example, the image processing device 140 corresponds to a so-called camera control unit (CCU) included in the control device 5317, and performs various types of processing related to a display of an image in the surgical navigation system 10.

In the processing related to a display of an image, as described with reference to FIG. 1, processing of causing a captured image to be displayed on the display device 5319, processing of causing a navigation image to be displayed on the display device 5319, and the like may be performed. For example, in the processing of causing a captured image to be displayed on the display device 5319, the CCU performs various types of signal processing on an image signal acquired by an imaging unit of the microscope unit 5303 of the observation device 5301 to generate image data for a display and to cause the image data to be displayed on the display device 5319. In the above-described signal processing, for example, various kinds of known signal processing such as development processing (demosaicing processing), high image quality processing (band emphasis processing, super resolution processing, noise reduction (NR) processing, and/or camera shake correction processing) and/or enlargement processing (i.e., electronic zoom processing) may be performed.

Note that the communication between the control device 5317 and the microscope unit 5303, as well as the communication between the control device 5317 and the first joint unit 5311a to the sixth joint unit 5311f, may be wired communication or wireless communication. In the case of wired communication, communication using electrical signals may be conducted, or optical communication may be conducted. In this case, the transmission cable used for wired communication may be configured as an electrical signal cable, optical fiber, or a composite cable of the two, in accordance with the communication method. Meanwhile, in the case of wireless communication, it is no longer necessary to lay down a transmission cable inside the operating room, and thus a situation in which the movement of medical staff inside the operating room is impeded by such a transmission cable may be resolved.

The control device 5317 may be a processor such as a central processing unit (CPU) or a graphics processing unit (GPU), a control board on which a processor and a storage element such as a memory are both mounted, or the like. As a result of the processor of the control device 5317 operating in accordance with a certain program, the various functions described above may be realized. Note that, in the example illustrated in the diagram, the control device 5317 is provided as a separate device from the observation device 5301, but the control device 5317 may also be unified with the observation device 5301, such as by being installed inside the base unit 5315 of the observation device 5301, for example. Alternatively, the control device 5317 may be made up of multiple devices. For example, by providing a control board or the like in the microscope unit 5303 and each of the first joint unit 5311a to the sixth joint unit 5311f of the arm unit 5309, and communicably connecting these control boards to each other, functions similar to the control device 5317 may be realized.

As described above, a specific configuration example of the observation device 5301 including the microscope unit 110 has been described. Note that, in the illustrated configuration example, the observation device 5301 has actuators provided in the joint units 5311a to 5311f of the arm unit 5309 thereof, and the arm unit 5309 can be driven, but the present embodiment is not limited to the example. For example, the microscope unit 110 may be supported by a so-called balance arm without having a drive mechanism.

5. Application Example

Figure 14:
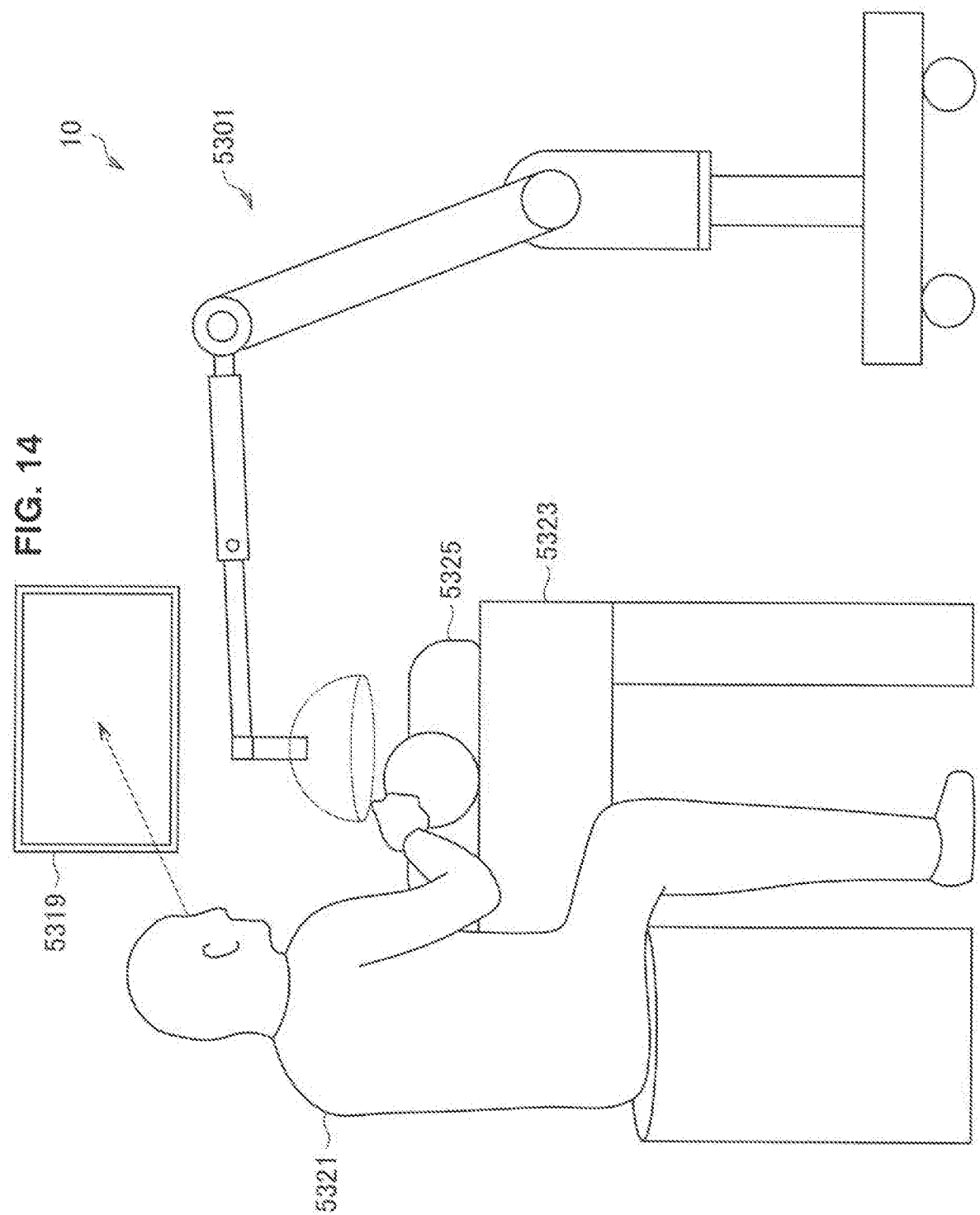
FIG. 14 is a diagram which shows a state of surgery using the surgical navigation system shown in FIGS. 1 and 13.

A state of surgery to which the surgical navigation system 10 shown in FIGS. 1 and 13 is applied will be described. FIG. 14 is a diagram which shows the state of surgery using the surgical navigation system 10 shown in FIGS. 1 and 13. In FIG. 14, a state in which a surgeon 5321 performs surgery on a patient 5325 on a patient bed 5323 using the surgical navigation system 10 is schematically shown. Note that illustration of the control device 5317 (that is, the image processing device 140) among constituents of the surgical navigation system 10 is omitted for the sake of simplicity, and the observation device 5301 is simplified and illustrated in FIG. 14.

As shown in FIG. 14, an image of an operating site photographed by the observation device 5301 is enlarged and displayed on the display device 5319 installed on a wall surface of a surgery room at the time of surgery. The display device 5319 is installed at a position facing the surgeon 5321, and the surgeon 5321, while observing the state of an operating site according to an image displayed on the display device 5319, performs various types of processing, for example, cutting off of an affected area, and the like, on the operating site.

Moreover, a navigation image generated by the image processing device 140 is displayed on the display device 5319 or another display device (not shown). The surgeon 5321 performs various types of processing on an operating site while referring to the navigation image. In the navigation image, for example, a lesion which is difficult to discern using a naked eye is displayed in an emphasized manner, and a positional relationship between a biological tissue including the lesion and a treatment tool is displayed in real time, and thus it is possible to perform surgery more smoothly by referring to the navigation image.

6. Supplement

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, an object on which matching processing is performed is set as an image representing a pattern of a blood vessel on a surface of a brain in the embodiment described above, but a technology of the present disclosure is not limited to the example. An image which is subjected to the matching processing may be an image showing a pattern on the surface of a brain, and may also be another pattern other than a blood vessel. For example, matching processing may be performed on an image representing a pattern of gyms of brain or sulcus of brain.

In addition, the technology of the present disclosure has been applied to a brain surgical operation in the embodiment described above, but the technology of the present disclosure is not limited to the example. The technology of the present disclosure can be applied to various types of surgical operations in which a navigation system is generally used. For example, the technology of the present disclosure can be used in various types of surgical operations performed on other sites such as laparoscopic surgery or endoscopic surgery. Similarly, even in a case in which the technology of the present disclosure is applied to these other surgical operations, a 3D model including a biological tissue including an operating site is generated, an amount of deformation of the biological tissue from before surgery is estimated, and a navigation image is generated using a 3D model updated on the basis of a result of the estimation. Then, at this time, a result of matching a predetermined pattern on a surface of a biological tissue can be used in the estimation processing of the amount of deformation of the biological tissue. The predetermined pattern may be a pattern of blood vessels existing on the surface of the biological tissue, and may also be a pattern of irregularities on the surface of the biological tissue itself.

In addition, the embodiment of the present disclosure on a medical purpose has been described in the above description, but the technology of the present disclosure is not limited to the example. The technology of the present disclosure may also be used in other fields on more general purposes. For example, the matching processing used in the present disclosure can be applied to matching between an existing map and an aerial photograph newly photographed. For example, it is possible to extract a difference from a result of the matching processing, and to use the difference at the time of newly creating a map and the like. Alternatively, for example, the matching processing used in the present disclosure can be applied to a monitoring system for fields or rice fields in an agriculture field. For example, an image of a field is periodically (for example, every day) photographed using a fixed camera, and matching processing is performed between an image in the past (for example, one day before) and a latest image to extract a difference. Growth condition and the like of crops is analyzed on the basis of the difference, and thereby it is possible to construct a system which automatically notifies an appropriate harvest time.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An image processing device including:

a matching unit that performs matching processing between a predetermined pattern on a surface of a 3D model of a biological tissue including an operating site generated on the basis of a preoperative diagnosis image and a predetermined pattern on a surface of the biological tissue included in a captured image during surgery;

a shift amount estimation unit that estimates an amount of deformation from a preoperative state of the biological tissue on the basis of a result of the matching processing and information regarding a three-dimensional position of a photographing region which is a region photographed during surgery on the surface of the biological tissue; and a 3D model update unit that updates the 3D model generated before surgery on the basis of the estimated amount of deformation of the biological tissue.

(2)

The image processing device according to (1), further including:

a display control unit that causes a display device to display a navigation image in which a display indicating a position of a treatment tool is added to the updated 3D model.

(3)

The image processing device according to (1) or (2), in which the biological tissue is a brain, the predetermined pattern is a pattern of brain surface blood vessels, and the shift amount estimation unit estimates an amount of brain shift which is an amount of deformation of brain with a craniotomy.

(4)

The image processing device according to any one of (1) to (3), in which the matching unit specifies a region corresponding to the photographing region on the surface of the 3D model by performing the matching processing, and the shift amount estimation unit estimates the amount of deformation on the basis of information regarding the specified region corresponding to the photographing region on the surface of the 3D model and information regarding a three-dimensional position of the photographing region.

(5)

The image processing device according to (4), in which the shift amount estimation unit sets a state in which a region corresponding to the photographing region on the surface of the 3D model is displaced in accordance with a three-dimensional position of the photographing region as an initial condition, and estimates the amount of deformation by calculating an amount of deformation of a calculation model corresponding to the 3D model using a finite element method.

(6)

The image processing device according to (5), in which the shift amount estimation unit sets a boundary condition in the calculation using the finite element method in accordance with a relationship between the biological tissue and another biological tissue in a periphery of the biological tissue.

(7)

The image processing device according to (6), in which the biological tissue is a brain, the other biological tissue is a cranial bone or dura mater, and a region corresponding to a contact part with the cranial bone or the dura mater in the calculation model is set as a fixed point which is not deformed in the boundary condition.

(8)

The image processing device according to any one of (1) to (7), in which information regarding a three-dimensional position of the photographing region is acquired on the basis of depth information added to a captured image obtained by photographing the photographing region.

(9)

The image processing device according to (8), in which the depth information is acquired on the basis of information regarding a focal distance at a time of photographing the photographing region.

(10)

The image processing device according to (8), in which the depth information is acquired on the basis of a detection value of a distance measurement sensor.

(11)

The image processing device according to (8), in which the depth information is acquired on the basis of disparity information obtained by a stereo camera.

(12)

The image processing device according to any one of (1) to (11), in which the matching unit calculates a matching error which is an index representing accuracy of matching when the matching processing is performed, and the image processing device further includes a warning control unit that causes a warning to be output in a case in which the matching error is equal to or greater than a predetermined threshold value.

(13)

The image processing device according to (12), in which the 3D model generation unit generates a 3D model of the biological tissue again on the basis of a diagnostic image newly acquired in a case in which the warning is output.

(14)

An image processing method including:

performing, by a processor, matching processing between a predetermined pattern on a surface of a 3D model of a biological tissue including an operating site generated on the basis of a preoperative diagnosis image and a predetermined pattern on a surface of the biological tissue included in a captured image during surgery;

estimating an amount of deformation from a preoperative state of the biological tissue on the basis of a result of the matching processing and information regarding a three-dimensional position of a photographing region which is a region photographed during surgery on the surface of the biological tissue; and updating the 3D model generated before surgery on the basis of the estimated amount of deformation of the biological tissue.

(15)

A program that causes a computer to execute an image processing method including:

performing matching processing between a predetermined pattern on a surface of a 3D model of a biological tissue including an operating site generated on the basis of a preoperative diagnosis image and a predetermined pattern on a surface of the biological tissue included in a captured image during surgery;

estimating an amount of deformation from a preoperative state of the biological tissue on the basis of a result of the matching processing and information regarding a three-dimensional position of a photographing region which is a region photographed during surgery on the surface of the biological tissue; and updating the 3D model generated before surgery on the basis of the estimated amount of deformation of the biological tissue.

(16)

A surgical navigation system including:

a microscope unit that photographs a biological tissue including an operating site of a patient during surgery, and acquires a captured image with depth information;

a position sensor that detects three-dimensional positions of the microscope unit, the patient, and a treatment tool;

a display device that displays a navigation image in which a display indicating a position of the treatment tool is added to a 3D model of the biological tissue; and an image processing device that causes the display device to display the navigation image, in which the image processing device includes a matching unit that performs matching processing between a predetermined pattern on a surface of the 3D model generated on the basis of a preoperative diagnosis image and a predetermined pattern on a surface of the biological tissue included in a captured image during surgery, a shift amount estimation unit that estimates an amount of deformation from a preoperative state of the biological tissue on the basis of a result of the matching processing and information regarding a three-dimensional position of a photographing region which is a region photographed during surgery by the microscope unit on the surface of the biological tissue, a 3D model update unit that updates the 3D model generated before surgery on the basis of the estimated amount of deformation of the biological tissue, and a display control unit that causes the display device to display the navigation image using the updated 3D model, in which information regarding a three-dimensional position of the photographing region is acquired on the basis of a result of detection by the position sensor and depth information of a captured image by the microscope unit.

REFERENCE SIGNS LIST

10 surgical navigation system
110 microscope unit
120 display device
130 position sensor
140 image processing device
141 3D model generation unit
142 matching unit
143 brain shift amount estimation unit
144 3D model update unit
145 display control unit
146 warning control unit

The invention claimed is:

1. An image processing device, comprising:
a processor configured to:
generate a first three-dimensional (3D) model of a first biological tissue based on a first preoperative diagnosis image of an operating site;
perform a matching process between a first determined pattern on a surface of the first 3D model of the first biological tissue and a second determined pattern on a surface of the first biological tissue included in an intraoperative image captured at a time of surgery;
specify a region of the first 3D model that corresponds to a photographing region photographed on the surface of the first 3D model at the time of the surgery, wherein the region is specified based on the matching process;
set a state in which the specified region corresponding to the photographing region is displaced in accordance with a three-dimensional position of the photographing region as an initial condition;
estimate an amount of deformation from a preoperative state of the first biological tissue by calculation of an amount of deformation of a calculation model corresponding to the first 3D model using a finite element method, wherein
the estimation of the amount of deformation of the first biological tissue is based on the initial condition, information regarding the specified region, a and information regarding the three-dimensional position of the photographing region; and
update the first 3D model, generated before the surgery, based on the estimated amount of deformation of the first biological tissue.

2. The image processing device according to claim 1, wherein the processor is further configured to control a display device to display a navigation image including a treatment tool at a determined position of the updated first 3D model.

3. The image processing device according to claim 1, wherein
the first biological tissue is a brain,
the first determined pattern is a pattern of brain surface blood vessels, and
the processor is further configured to estimate an amount of brain shift which is the amount of deformation of the brain with a craniotomy.

4. The image processing device according to claim 1, wherein the processor is further configured to set a boundary condition in the calculation of the amount of deformation using the finite element method in accordance with a relationship between the first biological tissue and a second biological tissue in a periphery of the first biological tissue.

5. The image processing device according to claim 4, wherein
the first biological tissue is a brain,
the second biological tissue is one of a cranial bone or dura mater, and a region corresponding to a contact part with the one of the cranial bone or the dura mater in the calculation model is set as a fixed point which is not deformed in the boundary condition.

6. The image processing device according to claim 1, wherein the processor is further configured to acquire the information regarding the three-dimensional position of the photographing region based on depth information included in the intraoperative image.

7. The image processing device according to claim 6, wherein the processor is further configured to acquire the depth information based on information regarding a focal distance at a time of capture of the photographing region.

8. The image processing device according to claim 6, wherein the processor is further configured to acquire the depth information based on a detection value of a distance measurement sensor.

9. The image processing device according to claim 6, wherein the processor is further configured to acquire the depth information based on disparity information obtained by a stereo camera.

10. The image processing device according to claim 1, wherein
the processor is further configured to:
calculate a matching error which is an index that represents accuracy of a match between the first determined pattern and the second determined pattern, wherein the calculation of the matching error is based on the matching process; and
output a warning in a case in which the matching error is one of equal to or greater than a determined threshold value.

11. The image processing device according to claim 10, wherein
the processor is further configured to:
acquire a second preoperative diagnosis image in a case where the warning is output; and
generate a second 3D model of the first biological tissue based on the second preoperative diagnosis image.

12. An image processing method, comprising:
generating, by a processor, a three-dimensional (3D) model of a biological tissue based on a preoperative diagnosis image of an operating site;
performing, by the processor, a matching process between a first determined pattern on a surface of the 3D model of the biological tissue and a second determined pattern on a surface of the biological tissue included in an intraoperative image captured at a time of surgery;
specifying, by the processor, a region of the 3D model that corresponds to a photographing region photographed on the surface of the 3D model at the time of the surgery, wherein the region is specified based on the matching process;
setting, by the processor, a state in which the specified region corresponding to the photographing region is displaced in accordance with a three-dimensional position of the photographing region as an initial condition;
estimating, by the processor, an amount of deformation from a preoperative state of the biological tissue by calculation of an amount of deformation of a calculation model corresponding to the 3D model using a finite element method, wherein
the estimation of the amount of deformation of the biological tissue is based on the initial condition, information regarding the specified region, and information regarding the three-dimensional position of the photographing region; and
updating, by the processor, the 3D model, generated before the surgery, based on the estimated amount of deformation of the biological tissue.

13. A non-transitory computer-readable medium having stored thereon, computer-executable instructions which, when executed by a processor, cause the processor to execute operations, the operations comprising:
generating a three-dimensional (3D) model of a biological tissue based on a preoperative diagnosis image of an operating site;
performing a matching process between a first determined pattern on a surface of the 3D model of the biological tissue and a second determined pattern on a surface of the biological tissue included in an intraoperative image captured at a time of surgery;
specifying a region of the 3D model that corresponds to a photographing region photographed on the surface of the 3D model at the time of the surgery, wherein the region is specified based on the matching process;
setting a state in which the specified region corresponding to the photographing region is displaced in accordance with a three-dimensional position of the photographing region as an initial condition;
estimating an amount of deformation from a preoperative state of the biological tissue by calculation of an amount of deformation of a calculation model corresponding to the 3D model using a finite element method, wherein
the estimation of the amount of deformation of the biological tissue is based on the initial condition, information regarding the specified region, and information regarding the three-dimensional position of the photographing region; and
updating the 3D model, generated before the surgery, based on the estimated amount of deformation of the biological tissue.

14. A surgical navigation system, comprising:
a microscope unit configured to:
photograph a biological tissue of an operating site of a patient at a time of surgery; and
acquire an intraoperative image with depth information at the time of the surgery;
a position sensor configured to detect a three-dimensional position of the microscope unit, a three-dimensional position of the patient, and a three-dimensional position of a treatment tool;
a display device configured to display a navigation image; and
an image processing device, wherein the image processing device includes a processor configured to:
generate a three-dimensional (3D) model of the biological tissue based on a preoperative diagnosis image of the operating site;
perform a matching process between a first determined pattern on a surface of the 3D model and a second determined pattern on a surface of the biological tissue included in the intraoperative image captured at the time of the surgery;
specify a region of the 3D model that corresponds to a photographing region photographed on the surface of the 3D model at the time of the surgery, wherein the region is specified based on the matching process;
set a state in which the specified region corresponding to the photographing region is displaced in accordance with a three-dimensional position of the photographing region as an initial condition;

estimate an amount of deformation from a preoperative state of the biological tissue by calculation of an amount of deformation of a calculation model corresponding to the 3D model using a finite element method, wherein
the estimation of the amount of deformation of the biological tissue is based on the initial condition, information regarding the specified region, and information regarding the three-dimensional position of the photographing region; and update the 3D model, generated before the surgery, based on the estimated amount of deformation of the biological tissue; and control the display device to display the navigation image including the treatment tool at a determined position in the updated 3D model, wherein the information regarding the three-dimensional position of the photographing region is acquired based on a result of detection by the position sensor and the depth information of the intraoperative image.

15. An image processing device, comprising:
a processor configured to:
generate a three-dimensional (3D) model of a biological tissue based on a preoperative diagnosis image of an operating site;

perform a matching process between a first determined pattern on a surface of the 3D model of the biological tissue and a second determined pattern on a surface of the biological tissue included in an intraoperative image captured at a time of surgery;

estimate an amount of deformation from a preoperative state of the biological tissue, wherein
the estimation of the amount of deformation of the biological tissue is based on a result of the matching process and information regarding a three-dimensional position of a photographing region photographed on the surface of the 3D model at the time of the surgery, the information regarding the three-dimensional position of the photographing region is based on depth information added to a captured image of the photographing region, and the depth information is based on disparity information obtained by a stereo camera; and update the 3D model, generated before the surgery, based on the estimated amount of deformation of the biological tissue.

16. An image processing device, comprising:
a processor configured to:
generate a three-dimensional (3D) model of a biological tissue based on a preoperative diagnosis image of an operating site;

perform a matching process between a first determined pattern on a surface of the 3D model of the biological tissue and a second determined pattern on a surface of the biological tissue included in an intraoperative image captured at a time of surgery;

estimate an amount of deformation from a preoperative state of the biological tissue, wherein the estimation of the amount of deformation of the biological tissue is based on a result of the matching process and information regarding a three-dimensional position of a photographing region photographed on the surface of the 3D model at the time of the surgery;

update the 3D model, generated before the surgery, based on the estimated amount of deformation of the biological tissue;

calculate a matching error which is an index representing accuracy of match between the first determined pattern and the second determined pattern, wherein the calculation of the matching error is based on the matching process; and cause a warning to be output in a case in which the matching error is one of equal to or greater than a determined threshold value.

* * * * *